US012796930B2

(12) United States Patent
Yokohama et al.

(10) Patent No.: US 12,796,930 B2
(45) Date of Patent: Nov. 17, 2026

(54) MEDICAL IMAGE DIAGNOSTIC SYSTEM, OPERATION METHOD OF MEDICAL IMAGE DIAGNOSTIC SYSTEM, AND VIDEO DISPLAY SYSTEM

(71) Applicant: FUJIFILM Healthcare Corporation, Chiba (JP)

(72) Inventors: Wataru Yokohama, Chiba (JP); Takeshi Nakayama, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 140 days.

(21) Appl. No.: 18/664,296

(22) Filed: May 15, 2024

(65) Prior Publication Data

US 2024/0382094 A1 Nov. 21, 2024

(30) Foreign Application Priority Data

May 16, 2023 (JP) ................................ 2023-081131

(51) Int. Cl.

*A61B 6/03* (2006.01)
*A61B 5/00* (2006.01)
*A61B 5/0205* (2006.01)

(52) U.S. Cl.

CPC .......... *A61B 5/0035* (2013.01); *A61B 5/0205* (2013.01); *A61B 5/7282* (2013.01); *A61B 5/7425* (2013.01)

(58) Field of Classification Search

CPC ......... A61B 6/032; A61B 6/037; A61B 6/461; A61B 5/055; A61B 5/0035; A61B 5/7425; A61B 5/742; A61B 5/7445; A61B 5/0205; A61B 5/7282; A61B 5/021; A61B 5/024; A61B 5/0816; A61B 5/318; A61B 5/02055; A61B 5/1452; A61B 5/14551

See application file for complete search history.

(56) References Cited

U.S. PATENT DOCUMENTS

2013/0162510 A1* 6/2013 Ohgishi ................ G09G 3/344 324/318
2014/0088405 A1* 3/2014 Assmann .............. A61B 5/053 600/411
2014/0350381 A1* 11/2014 Kim ................. A61M 5/16831 600/431

(Continued)

FOREIGN PATENT DOCUMENTS

EP 4124875 A1 * 2/2023 .......... G01R 33/283
JP 2018029763 3/2018
JP 2022000094 1/2022

*Primary Examiner* — Boniface N Nganga
(74) *Attorney, Agent, or Firm* — JCIPRNET

(57) ABSTRACT

Provided are a medical image diagnostic system, an operation method of a medical image diagnostic system, and a video display system which can display a video for a subject during an examination using an image diagnostic apparatus based on vital information of the subject. A medical image diagnostic system includes a projector that displays a video in an aspect visible to a subject during an MRI examination in a bore, a vital information detection device that detects vital information of the subject during the examination, and a processor, in which the processor acquires the vital information from the vital information detection device, and causes the projector to perform projection display of a predetermined video based on the acquired vital information.

14 Claims, 19 Drawing Sheets

(56) References Cited

U.S. PATENT DOCUMENTS

| | | | | |
|---|---|---|---|---|
| 2015/0045654 | A1* | 2/2015 | Lee | A61B 6/46<br>600/413 |
| 2016/0058397 | A1* | 3/2016 | Kim | A61B 5/055<br>600/418 |
| 2018/0353145 | A1* | 12/2018 | Simon | A61B 6/54 |
| 2020/0008703 | A1* | 1/2020 | Zeller | A61B 5/0205 |
| 2021/0393231 | A1 | 12/2021 | Nishijima | |

* cited by examiner

FIG. 19

| # | DETECTION EXAMPLE OF VITAL INFORMATION | STATE OF SUBJECT | DISPLAY CONTENT |
|---|---|---|---|
| 1 | SIGNIFICANT INCREASE IN HEAT RATE (PULSE) AND RESPIRATORY RATE | SUBJECT IS CONSCIOUS, BUT FEELS ANXIOUS OR IS NERVOUS BECAUSE HE OR SHE CANNOT ENDURE LONG-TERM EXAMINATION OR CLOSED SPACE. | CONFIRM INTENTION REGARDING WHETHER OR NOT TO BE ABLE TO CONTINUE EXAMINATION & DISPLAY VIDEO OF TECHNICIAN (OPERATOR) |
| 2 | SIGNIFICANT DECREASE IN SpO2 AND RESPIRATORY STOP | SUDDEN CHANGE WITH DETERIORATION IN VITAL SIGN, AND SUBJECT MAY BE ONLY HALF CONSCIOUS OR UNCONSCIOUS. | IMMEDIATELY DISPLAY VIDEO OF TECHNICIAN (OPERATOR), AND INCASE IN WHICH THERE IS NO RESPONSE OF PATIENT, STOP EXAMINATION |
| 3 | HEART RATE (PULSE) OR ELECTROCARDIOGRAM INFORMATION IS DISTURBED OR STIFFNESS OF FACIAL EXPRESSION APPEARS | ALTHOUGH IT IS GUESS, THERE IS POSSIBILITY THAT MR-COMPATIBLE PACEMAKER IS ERRONEOUSLY OPERATED OR ABNORMALITY OCCURS IN BODY. | CONFIRM INTENTION REGARDING WHETHER OR NOT TO BE ABLE TO CONTINUE EXAMINATION |
| 4 | SUDDEN CHANGE IN SpO2, DECREASE IN PULSE OR BLOOD PRESSURE (INCLUDING FACIAL PALLOR), OR INCREASE IN RESPIRATORY RATE APPEARS AFTER CONTRAST MEDIUM IS INJECTED | THERE IS CONCERN THAT SIDE EFFECT DUE TO CONTRAST MEDIUM APPEARS. | CONFIRM INTENTION REGARDING WHETHER OR NOT TO BE ABLE TO CONTINUE EXAMINATION & DISPLAY VIDEO OF TECHNICIAN (OPERATOR) |
| 5 | INCREASE IN BODY TEMPERATURE | BODY TEMPERATURE IS INCREASED DUE TO INCREASE IN SAR, AND BODY AROUND EXAMINATION PART IS HOT. | CONFIRM INTENTION REGARDING WHETHER OR NOT TO BE ABLE TO CONTINUE EXAMINATION |
| 6 | RESPIRATORY IS TEMPORARILY DISTURBED OR COUGHING OR SNEEZING IN STATE IN WHICH CONTRAST MEDIUM IS NOT INJECTED | IT'S NOT THAT SUBJECT DOESN'T FEEL PAIN DURING EXAMINATION, BUT SUBJECT THINKS TO CONTINUE EXAMINATION. DISTURBANCE, COUGHING, OR SNEEZING JUST HAS HAPPENED TO APPEAR. | NO DISPLAY |

MEDICAL IMAGE DIAGNOSTIC SYSTEM, OPERATION METHOD OF MEDICAL IMAGE DIAGNOSTIC SYSTEM, AND VIDEO DISPLAY SYSTEM

CROSS-REFERENCE TO RELATED APPLICATION

The present application claims priority under 35 U.S.C § 119 (a) to Japanese Patent Application No. 2023-081131 filed on May 16, 2023, which is hereby expressly incorporated by reference, in its entirety, into the present application.

BACKGROUND OF THE INVENTION

1. Field of the Invention

The present invention relates to a medical image diagnostic system, an operation method of a medical image diagnostic system, and a video display system, and particularly relates to a technique of displaying a video visible to a subject during an examination using an image diagnostic apparatus.

2. Description of the Related Art

An examination time for a subject using an image diagnostic apparatus, such as a magnetic resonance imaging apparatus (MRI apparatus) or an X-ray computed tomography (CT) apparatus, is relatively long, and is about 20 minutes to 30 minutes in a case of the MRI apparatus, and is about 5 minutes to 10 minutes in a simple examination and about 5 minutes to 20 minutes in a contrast examination in a case of the X-ray CT apparatus.

In addition, imaging using the MRI apparatus or the like is performed in a cylindrical imaging space called a "bore", and since body movement can be an image artifact during the examination, it is necessary to suppress the body movement as much as possible including breathing. The examination in which the subject suppresses the body movement for a long time in a closed space called a "bore" is stressful for the subject.

As a result, the subject may feel anxious, and have a poor physical condition due to an increase in a body temperature (having a fever), an increase in a heart rate, or a drug injection. Although there is a case in which an emergency switch is given to the subject, the subject may not push the emergency switch (may not sound an emergency buzzer) because the subject may have a psychological resistance to stop the examination. Further, an operator of the MRI apparatus or the like proceeds with the examination while looking at the subject whose consciousness is not clear in an emergency examination or the like, but the operator may not notice a change in the subject because the operator also concentrates on an operation screen.

JP2022-94A discloses a medical image diagnostic system that acquires vital information of a patient in an examination of the patient using an X-ray CT apparatus. In the medical image diagnostic system disclosed in JP2022-94A, in a case of controlling a transition of each of a plurality of steps included in a workflow for examining the patient, among the plurality of steps, first information indicating a preparation status of the patient in a first step is acquired, second information indicating permission of the transition from the first step to a second step is acquired, and the transition from the first step to the second step is controlled based on the first information and the second information.

Here, the vital information is used as information for determining a posture or an operation of the patient, such as whether or not the patient performs an operation of closing a door of a CT room or whether or not the patient lies down on a top plate of a bed device, among the plurality of steps included in the workflow.

JP2018-29763A discloses a medical image diagnostic system that projects two videos having different purposes to different positions, respectively. The medical image diagnostic system disclosed in JP2018-29763A projects a first video for the purpose of alleviating stress of a patient during an examination from one projector onto an inner wall of a bore of a medical image diagnostic apparatus, and projects a second video for the purpose of showing information related to imaging on the patient onto a surface (rear surface) of an exterior of a stand having an opening of the bore.

Here, the second video is a video having biological information such as electrocardiogram information, the body temperature, a respiratory rate, and a pulse rate of the patient, and information such as the operation screen, a reconstructed image, and an imaging condition in the medical image diagnostic system, and is a video necessary for a medical worker.

SUMMARY OF THE INVENTION

JP2022-94A and JP2018-29763A disclose a technique of acquiring the vital information of the subject during the examination using the image diagnostic apparatus, but do not disclose a technique of displaying a predetermined video for the subject based on the vital information.

The present invention has been made in view of such circumstances, and an object thereof is to provide a medical image diagnostic system, an operation method of a medical image diagnostic system, and a video display system which can display a video for a subject during an examination using an image diagnostic apparatus based on vital information of the subject.

A first aspect of the present invention relates to a medical image diagnostic system comprising: a video display device that displays a video in an aspect visible to a subject during an examination of the subject using an image diagnostic apparatus; a vital information detection device that detects vital information of the subject during the examination; and a processor, in which the processor acquires the vital information from the vital information detection device, and causes the video display device to display a predetermined video based on the acquired vital information.

According to the first aspect of the present invention, it is possible to display the predetermined video for the subject on the video display device based on the vital information of the subject during the examination.

A second aspect of the present invention relates to the medical image diagnostic system according to the first aspect, in which the processor preferably determines whether or not the vital information or an amount of change in the vital information exceeds a first threshold value, and causes the video display device to display a video for confirming an intention of the subject regarding whether or not to be able to continue the examination using the image diagnostic apparatus, in a case in which it is determined that the vital information or the amount of change in the vital information exceeds the first threshold value.

In a case in which the vital information of the subject during the examination or the amount of change in the vital information exceeds the first threshold value, it is considered that the subject feels the poor physical condition. According to the second aspect of the present invention, in a case in which the vital information of the subject or the amount of change in the vital information of the subject during the examination exceeds the first threshold value, the video for confirming the intention of the subject regarding whether or not to be able to continue the examination is displayed on the video display device.

A third aspect of the present invention relates to the medical image diagnostic system according to the first or second aspect, preferably further comprising: a first camera that images an operator who operates the image diagnostic apparatus, in which the processor determines whether or not the vital information or an amount of change in the vital information exceeds a second threshold value, and causes the video display device to display a video of the operator captured by the first camera in a case in which it is determined that the vital information or the amount of change in the vital information exceeds the second threshold value.

In a case in which the vital information of the subject during the examination exceeds the first threshold value, it is considered that the subject feels the poor physical condition. According to the third aspect of the present invention, in a case in which the vital information of the subject during the examination exceeds the second threshold value, the video of the operator is displayed on the video display device to reduce the psychological burden on the subject.

A fourth aspect of the present invention relates to the medical image diagnostic system according to any one of the first to third aspects, preferably further comprising: a second speaker that transmits a voice, which is detected by a first microphone and uttered by an operator who operates the image diagnostic apparatus, or an automatic voice to the subject during the examination. As a result, it is possible to reduce the psychological burden on the subject through the voice.

A fifth aspect of the present invention relates to the medical image diagnostic system according to the second aspect, preferably further comprising: an intention detection device that detects an intention of the subject with respect to the video for confirming the intention of the subject; and an intention confirmation device that transmits a detection result detected by the intention detection device to an operator who operates the image diagnostic apparatus. As a result, it is possible to communicate between the subject and the operator, and it is possible to reduce the psychological burden on the subject.

A sixth aspect of the present invention relates to the medical image diagnostic system according to the fifth aspect, in which the intention detection device is preferably a second microphone that detects a voice of the subject during the examination, a second camera that images the subject, or an operation device operated by the subject, and the intention confirmation device is a first speaker that transmits the voice detected by the second microphone to the operator who operates the image diagnostic apparatus, an utterance recognition device that analyzes a movement of lips of the subject from a video of the subject captured by the second camera to recognize an utterance content of the subject, a detection device that analyzes a movement of a hand or a finger of the subject from the video of the subject captured by the second camera to detect the intention of the subject, or an notification device that outputs an operation result of the operation device.

A seventh aspect of the present invention relates to the medical image diagnostic system according to any one of the first to seventh aspects, in which the vital information of the subject is preferably one or more of electrocardiogram information, a heart rate, a blood oxygen saturation concentration, a respiratory rate, a blood pressure, or a body temperature.

An eighth aspect of the present invention relates to the medical image diagnostic system according to any one of the first to seventh aspects, in which the vital information detection device preferably includes a third camera that images the subject during the examination, and analyzes an image captured by the third camera to detect at least one of a heart rate or a respiratory rate of the subject.

A ninth aspect of the present invention relates to the medical image diagnostic system according to any one of the first to eighth aspects, in which the vital information detection device preferably includes at least one of an electrocardiogram (ECG) sensor that detects electrocardiogram information and/or a heart rate, a peripheral oxygen saturation (SpO2) sensor that measures a blood oxygen saturation concentration, a bellows that detects a respiratory rate, a pressure sensor that detects a blood pressure, an optical camera that is able to detect a body temperature, an infrared camera, or a thermography.

A tenth aspect of the present invention relates to the medical image diagnostic system according to any one of the first to ninth aspects, in which the vital information detection device is preferably a signal processing apparatus that detects the vital information based on an image captured by the image diagnostic apparatus, an NMR signal obtained from a magnetic resonance imaging apparatus in a case in which the image diagnostic apparatus is the magnetic resonance imaging apparatus, or a pulse sequence.

An eleventh aspect of the present invention relates to the medical image diagnostic system according to any one of the first to tenth aspects, in which the video display device is preferably a projector that performs projection onto a screen visible to the subject, a head-up display, a head-mounted display, a liquid crystal display, or an organic EL display.

A twelfth aspect of the present invention relates to the medical image diagnostic system according to any one of the first to eleventh aspects, in which the image diagnostic apparatus preferably includes a magnetic resonance imaging apparatus, an X-ray CT apparatus, a PET apparatus, a radiation therapy apparatus, or a particle beam therapy apparatus.

A thirteenth aspect of the present invention relates to an operation method of a medical image diagnostic system including a video display device that displays a video in an aspect visible to a subject during an examination of the subject using an image diagnostic apparatus, a vital information detection device that detects vital information of the subject during the examination, and a processor, the operation method comprising: a step of acquiring, via the processor, the vital information of the subject from the vital information detection device; and a step of causing, via the processor, the video display device to display a predetermined video based on the acquired vital information.

A fourteenth aspect of the present invention relates to the operation method of a medical image diagnostic system according to the thirteenth aspect, preferably further comprising: a step of determining, via the processor, whether or not the acquired vital information or an amount of change in the vital information exceeds a first threshold value; and a step of causing, via the processor, the video display device to display a video for confirming an intention of the subject regarding whether or not to be able to continue the examination using the image diagnostic apparatus, in a case in which it is determined that the vital information or the amount of change in the vital information exceeds the first threshold value.

A fifteenth aspect of the present invention relates to the operation method of a medical image diagnostic system according to the thirteenth or fourteenth aspect, in which a first camera that images an operator who operates the image diagnostic apparatus is preferably further included, and the operation method preferably further comprises: a step of determining, via the processor, whether or not the vital information or an amount of change in the vital information exceeds a second threshold value; and a step of causing, via the processor, the video display device to display a video of the operator captured by the first camera in a case in which it is determined that the vital information or the amount of change in the vital information exceeds the second threshold value.

A sixteenth aspect of the present invention relates to a video display system comprising: a video display device that displays a video in an aspect visible to a subject during an examination of the subject using an image diagnostic apparatus; a vital information detection device that detects vital information of the subject during the examination; and a processor, in which the processor acquires the vital information from the vital information detection device, and causes the video display device to display a predetermined video based on the acquired vital information.

According to the present invention, it is possible to display the predetermined video for the subject on the video display device based on the vital information of the subject during the examination using the image diagnostic apparatus, and it is possible to reduce the psychological burden on the subject.

BRIEF DESCRIPTION OF THE DRAWINGS

FIG. 5 is a view showing an example of a display screen of a display device that displays vital information and the like.

FIG. 6 is a view showing another example of the display screen of the display device that displays the vital information and the like.

FIG. 7 is a view showing still another example of the display screen of the display device that displays the vital information and the like.

FIG. 19 is a table showing a relationship between a detection example of the vital information, a state of the subject, and a display content of the video displayed on the subject side.

DESCRIPTION OF THE PREFERRED EMBODIMENTS

Hereinafter, preferred embodiments of a medical image diagnostic system, an operation method of a medical image diagnostic system, and a video display system according to an embodiment of the present invention will be described with reference to the accompanying drawings.

Figure 1:
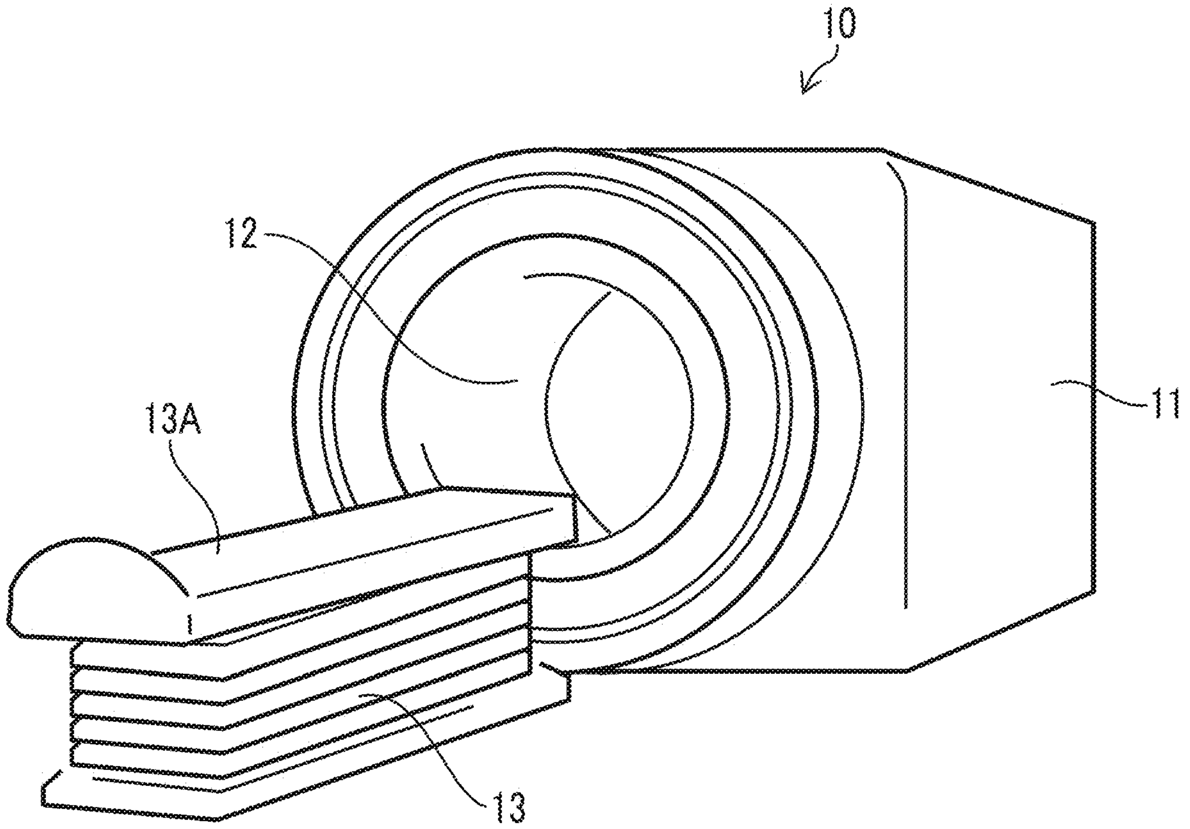
FIG. 1 is a perspective view showing an example of an image diagnostic apparatus to which a medical image diagnostic system according to an embodiment of the present invention is applied.

FIG. 1 is a perspective view showing an example of an image diagnostic apparatus to which the medical image diagnostic system according to the embodiment of the present invention is applied.

An image diagnostic apparatus shown in FIG. 1 is a magnetic resonance imaging apparatus (MRI apparatus) 10, and comprises a gantry 11 and a bed 13 comprising a top plate 13A disposed on a front side of a bore 12 that is a cylindrical imaging space provided in the gantry 11.

The image diagnostic apparatus according to the present example is the MRI apparatus 10, but the present invention is not limited thereto, and includes an X-ray CT apparatus, a positron emission tomography (PET) apparatus, a radiation therapy apparatus, or a particle beam therapy apparatus. The present invention is suitable for an apparatus in which the examination time and the treatment time are relatively long.

Figure 2:
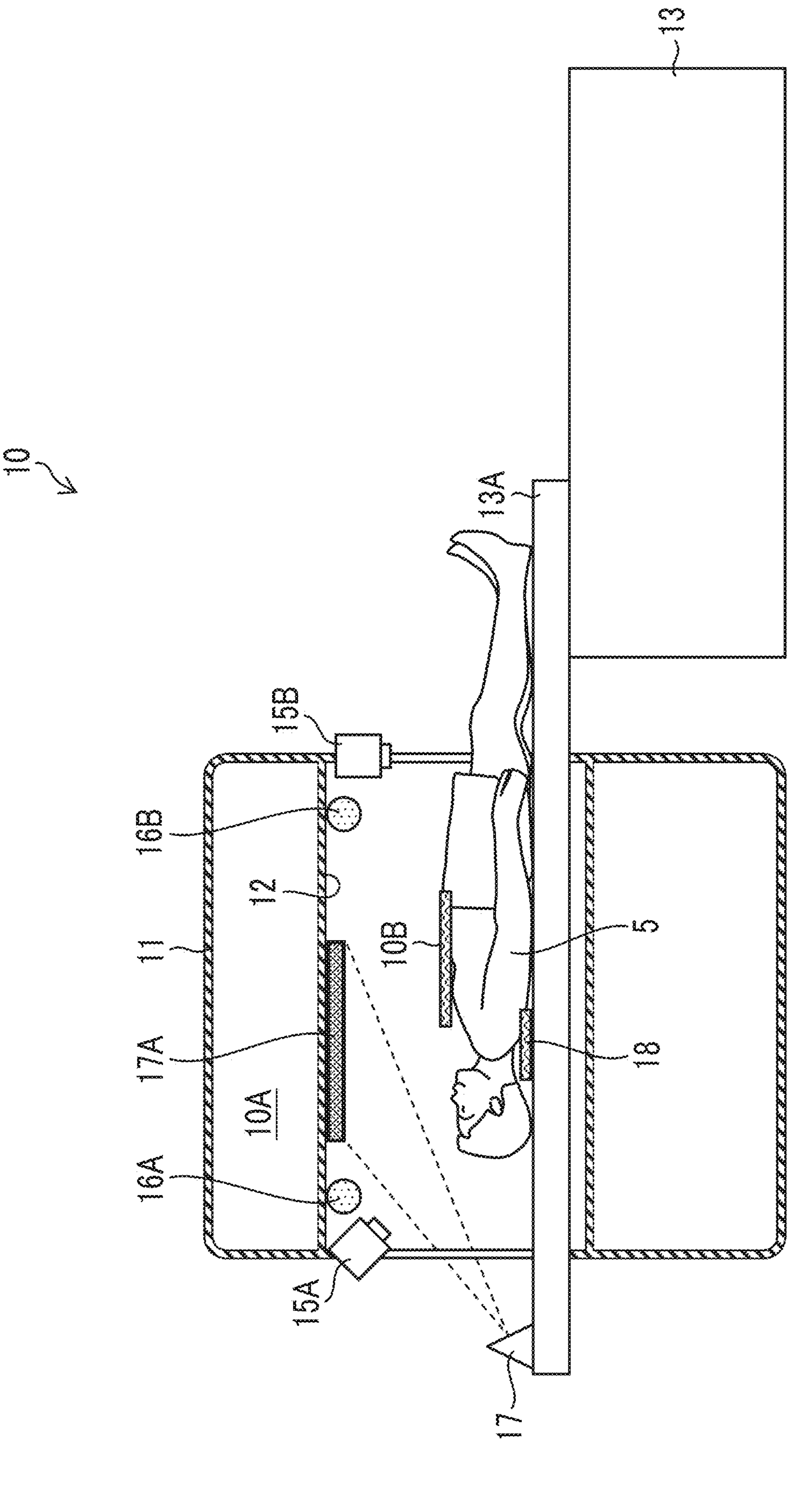
FIG. 2 is a schematic cross-sectional view of an MRI apparatus shown in FIG. 1.

FIG. 2 is a schematic cross-sectional view of the MRI apparatus shown in FIG. 1.

In FIG. 2, an MRI magnet 10A and various coils are provided on the gantry 11, and a subject 5 lying face up on the top plate 13A is moved so that the examination part of the subject 5 is located at the center of the static magnetic field in the bore 12 by moving the top plate 13A to the bore 12. A radio frequency (RF) coil 10B for receiving free induction decay (FID) from a human body is disposed at the examination part of the subject 5. In the present example, the abdomen of the subject 5 is the examination part, and the RF coil 10B is disposed on the abdomen.

A second camera 15 (15A and 15B) and a second microphone 16 (16A and 16B), which are visible light cameras, are disposed at the upper portion of both ends of the bore 12. It should be noted that, in FIG. 2, the second camera 15A and the second microphone 16A are disposed at the upper portion of the left end of the bore 12, and the second camera 15B and the second microphone 16B are disposed at the upper portion of the right end of the bore 12.

Each of the two second cameras 15A and 15B images the subject 5 and outputs a moving image (video), and at least one of the second camera 15A or the second camera 15B images a video including a face region of the subject 5.

Further, each of the two second microphones 16A and 16B detects a voice uttered by the subject 5. It is preferable that the second microphones 16A and 16B are non-magnetic microphones using a piezoelectric ceramic that is a non-magnetic material in a sound receiving element portion.

A projector 17 is provided at one end (in FIG. 2, the left end) of the top plate 13A, and the projector 17 projects the video onto a screen 17A that is provided in a ceiling portion in the bore 12. The projector 17 functions as a video display device that displays a video in an aspect visible to the subject 5 during the examination using the MRI apparatus 10, and the subject 5 can visually recognize the video projected onto the screen 17A during the examination. It should be noted that the ceiling portion in the bore 12 may be used as a screen without providing the screen 17A.

In FIG. 2, 18 indicates a vital information detection device that measures one or more of electrocardiogram information, a heart rate (pulse rate), a blood oxygen saturation concentration, a respiratory rate, a blood pressure, or a body temperature of the subject 5. The vital information detection device 18 is not limited to being disposed on the back portion of the subject 5.

Specific examples of the vital information detection device 18 include at least one of an ECG sensor that detects electrocardiogram information and/or a heart rate, an SpO2 sensor that measures a blood oxygen saturation concentration, a bellows that detects a respiratory rate, a pressure sensor that detects a blood pressure, an optical camera that is able to detect a body temperature, an infrared camera, or a thermography.

Further, a signal processing apparatus that detects the vital information based on an MRI image captured by the image diagnostic apparatus (MRI apparatus 10), a nuclear magnetic resonance (NMR) signal (a signal itself acquired in an MRI examination in a case in which the image diagnostic apparatus is the MRI apparatus), or a pulse sequence may be used as the vital information detection device. Other sensors (an optical sensor, an ultrasound sensor, and the like) and a combination thereof can be used as the vital information detection device.

For example, the movement of the diaphragm and the movement of the heart can be detected from the MRI image to detect the respiratory rate and the heart rate. It should be noted that these movement detections are used to reduce artifacts of the MRI images. In addition, the vital information may be detected by using a machine learning model into which the video, the MRI image, or the like obtained by imaging the subject is input.

Figure 3A:
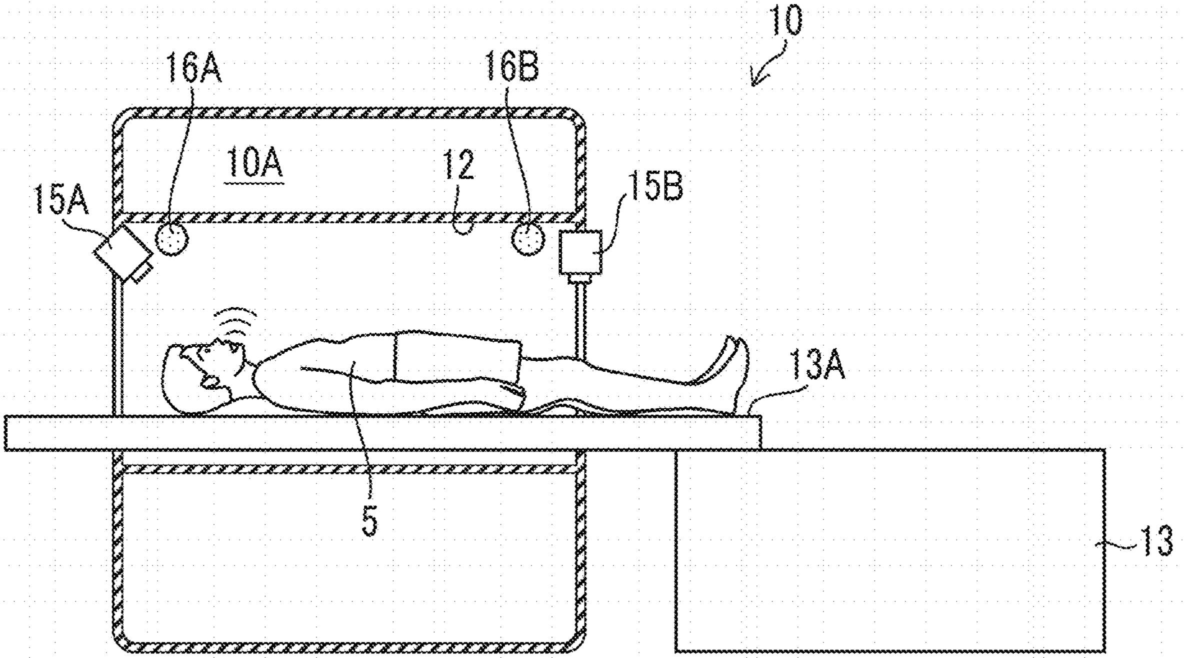
FIGS. 3A and 3B are views showing switching of a direction of a body of a subject with respect to the MRI apparatus.
Figure 3B:
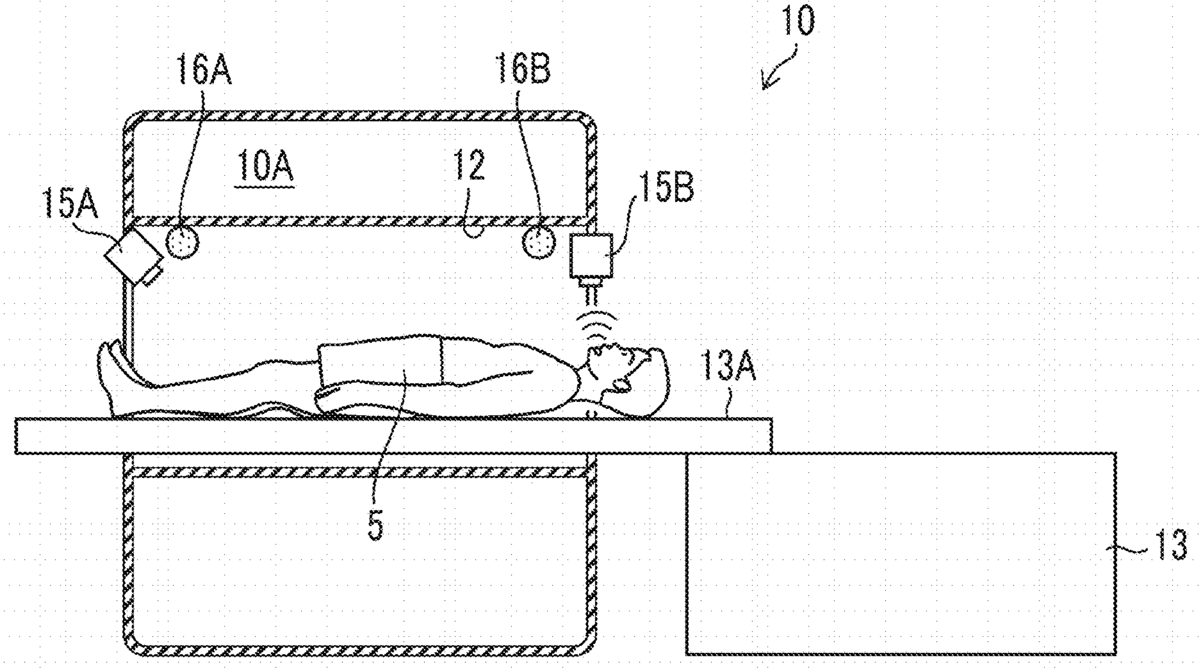

FIGS. 3A and 3B are views showing switching of a direction of a body of the subject with respect to the MRI apparatus.

FIG. 3A shows a case in which the subject 5 enters the bore 12 from the head (head first), and FIG. 3B shows a case in which the subject 5 enters the bore 12 from the foot (foot first).

The head first or the foot first is selected depending on the examination part of the subject 5. In the present example, in order to perform the imaging of the face region of the subject 5 and the detection of the voice regardless of whether the head first or the foot first is selected, the second cameras 15A and 15B and the second microphones 16A and 16B are provided at both end portions of the bore 12, respectively.

It should be noted that the second camera 15 (15A and 15B) and the second microphone 16 (16A and 16B) are two in the present example, but are not limited thereto, and may be one or three or more. In addition, the second camera 15 and the second microphone 16 are not limited to being disposed in the MRI apparatus 10, and may be disposed in the vicinity of the MRI apparatus 10.

Figure 4:
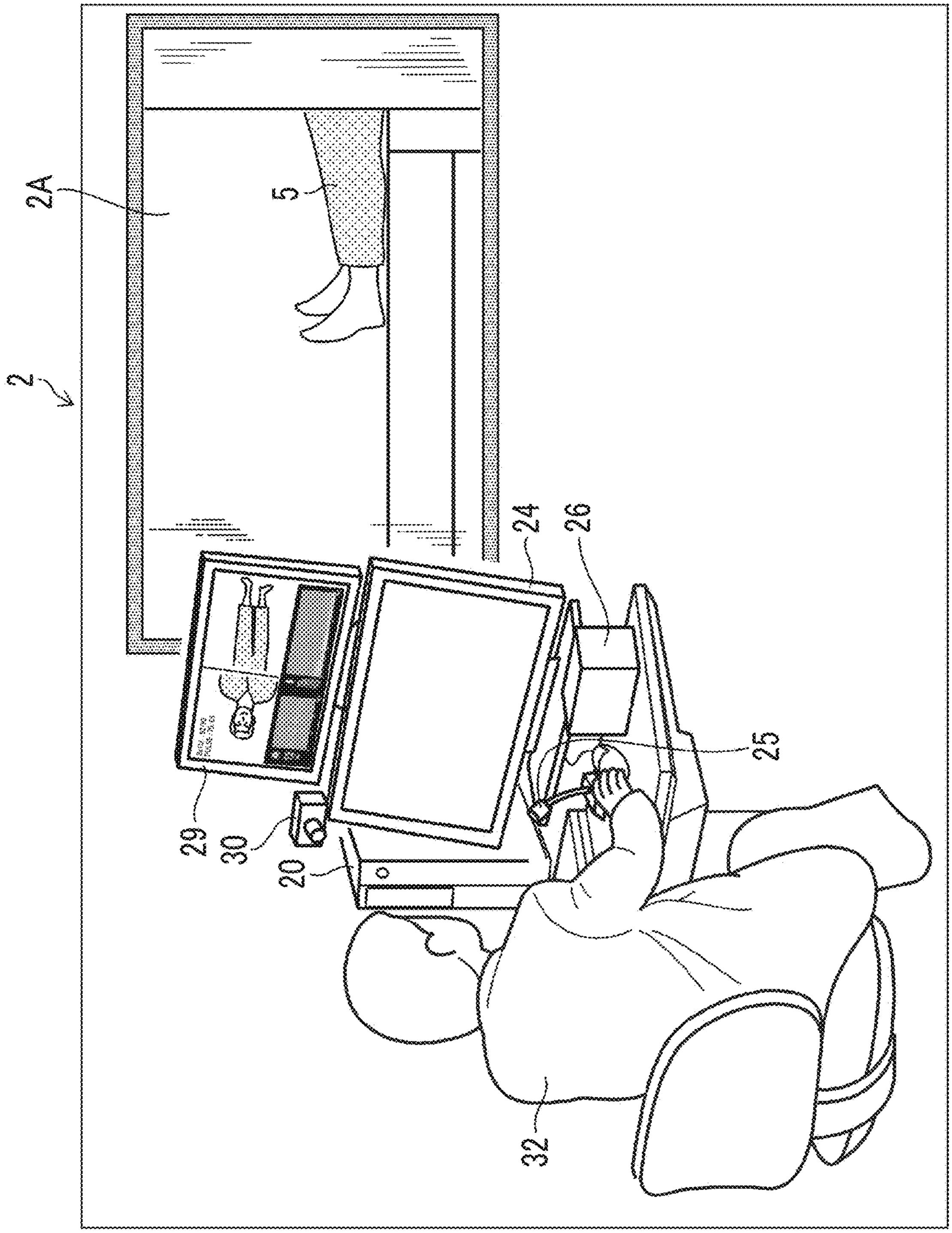
FIG. 4 is a view showing a state inside an operation room in which the MRI apparatus is operated.

FIG. 4 is a view showing a state inside an operation room in which the MRI apparatus is operated.

As shown in FIG. 4, a signal processing apparatus 20 that controls the MRI apparatus 10 installed in the examination room, processes the NMR signal output from the MRI apparatus 10, and generates the MRI image is installed in the operation room 2.

The signal processing apparatus 20 can be configured by using a computer. The computer applied to the signal processing apparatus 20 may be a personal computer or may be a workstation. An operator 32 can control the operation of the MRI apparatus 10 through the signal processing apparatus 20 by using an operation unit 28 such as a keyboard and a mouse.

In addition, the signal processing apparatus 20 according to the present example has a part of the functions of the medical image diagnostic system according to the embodiment of the present invention (that is, a function as a “video display system” that displays a video or the like for the subject), but the details thereof will be described below.

The signal processing apparatus 20 comprises a display device 24 that displays the MRI image or the like, a first microphone 25 that detects a voice of the operator 32, and a first speaker 26 that generates a voice or the like uttered by the subject 5 during the examination.

In addition, in FIG. 4, 2A indicates a window for the operator 32 to see the inside of the examination room. 29 indicates a display device that displays the video captured by the second cameras 15A and 15B, the vital information, and the like, and 30 indicates a first camera that images the operator 32.

Figure 5:
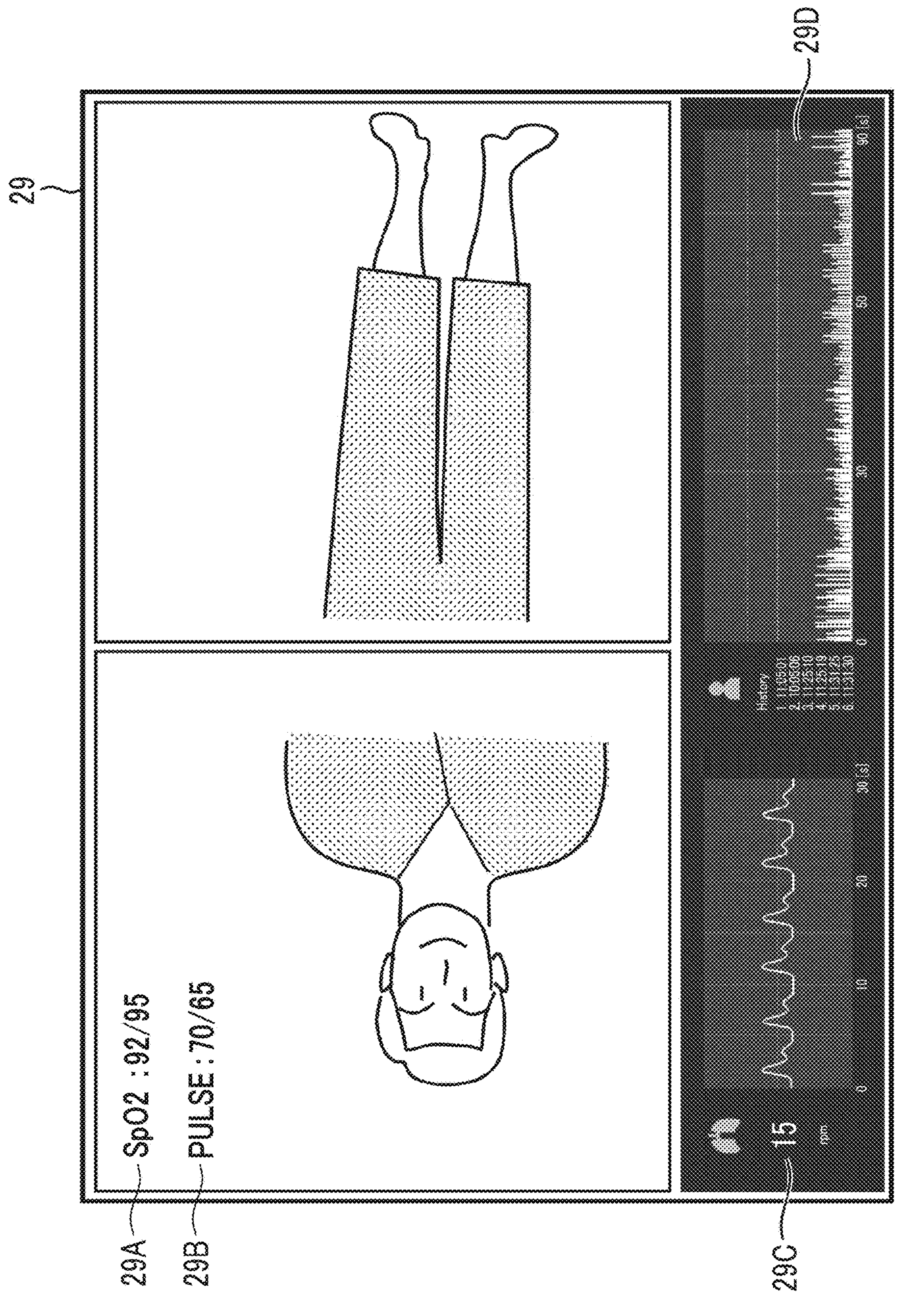

FIG. 5 is a view showing an example of a display screen of the display device that displays the vital information or the like, and is an enlarged view of the display screen of the display device 29 shown in FIG. 4.

As shown in FIG. 5, the display screen of the display device 29 displays the video of the subject 5 captured by the second cameras 15A and 15B, and in the present example, a video of an upper body side of the subject 5 captured by the second camera 15A and a video of a lower body side of the subject 5 captured by the second camera 15B are displayed.

Further, as the vital information of the subject 5 during the examination, a blood oxygen saturation concentration (SpO2) 29A, a pulse rate 29B, a respiratory rate 29C, a body movement (vibration waveform) 29D, and the like are displayed.

The operator 32 can observe a state of the subject 5 during the examination (for example, facial pallor, stiffness of a facial expression, movement of eyes, and the like) from the display screen of the display device 29, and can confirm the vital information of the subject 5. It should be noted that FIG. 5 shows the vital information and the like at the start of the examination of the subject 5.

Figure 6:
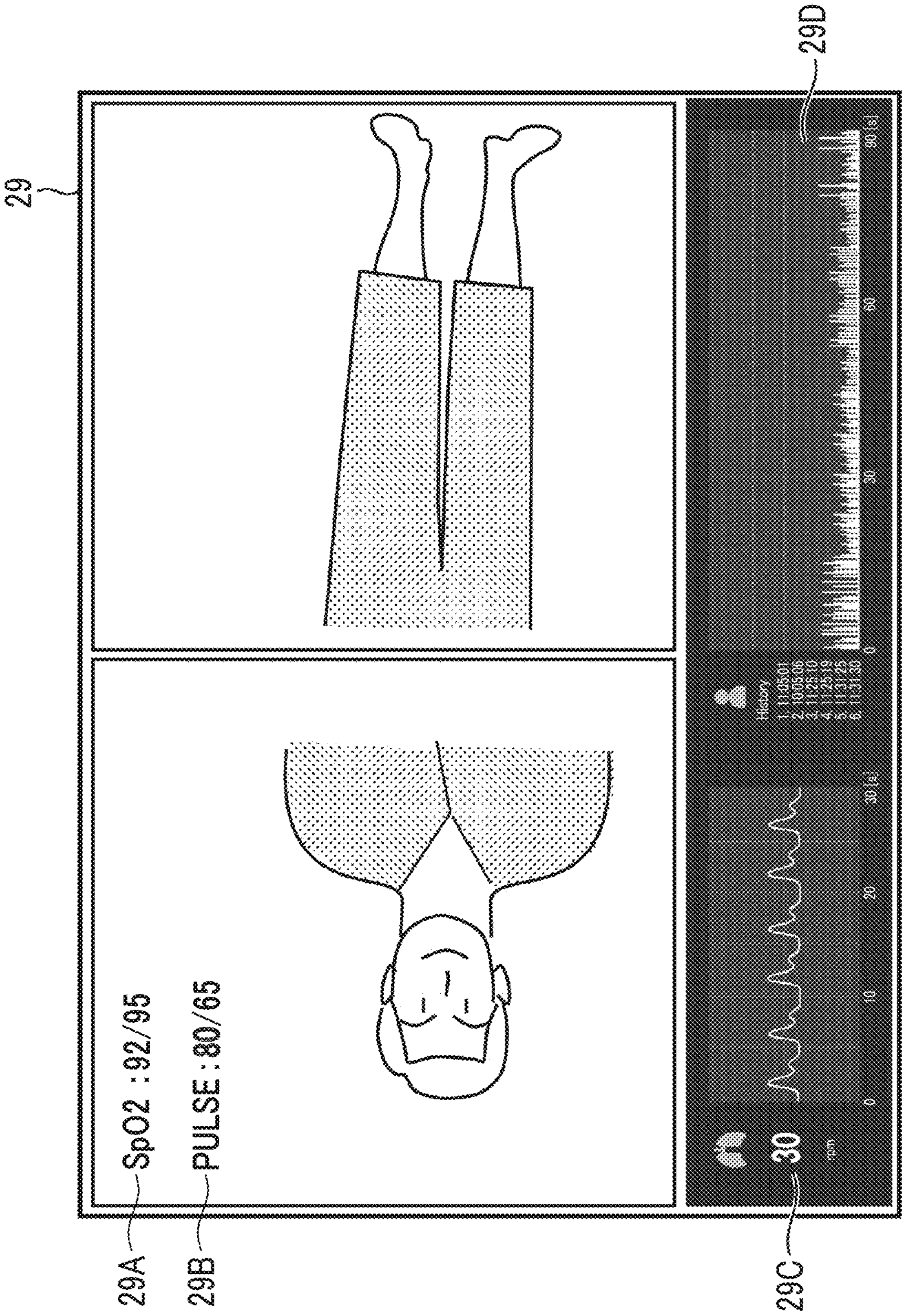
Figure 7:
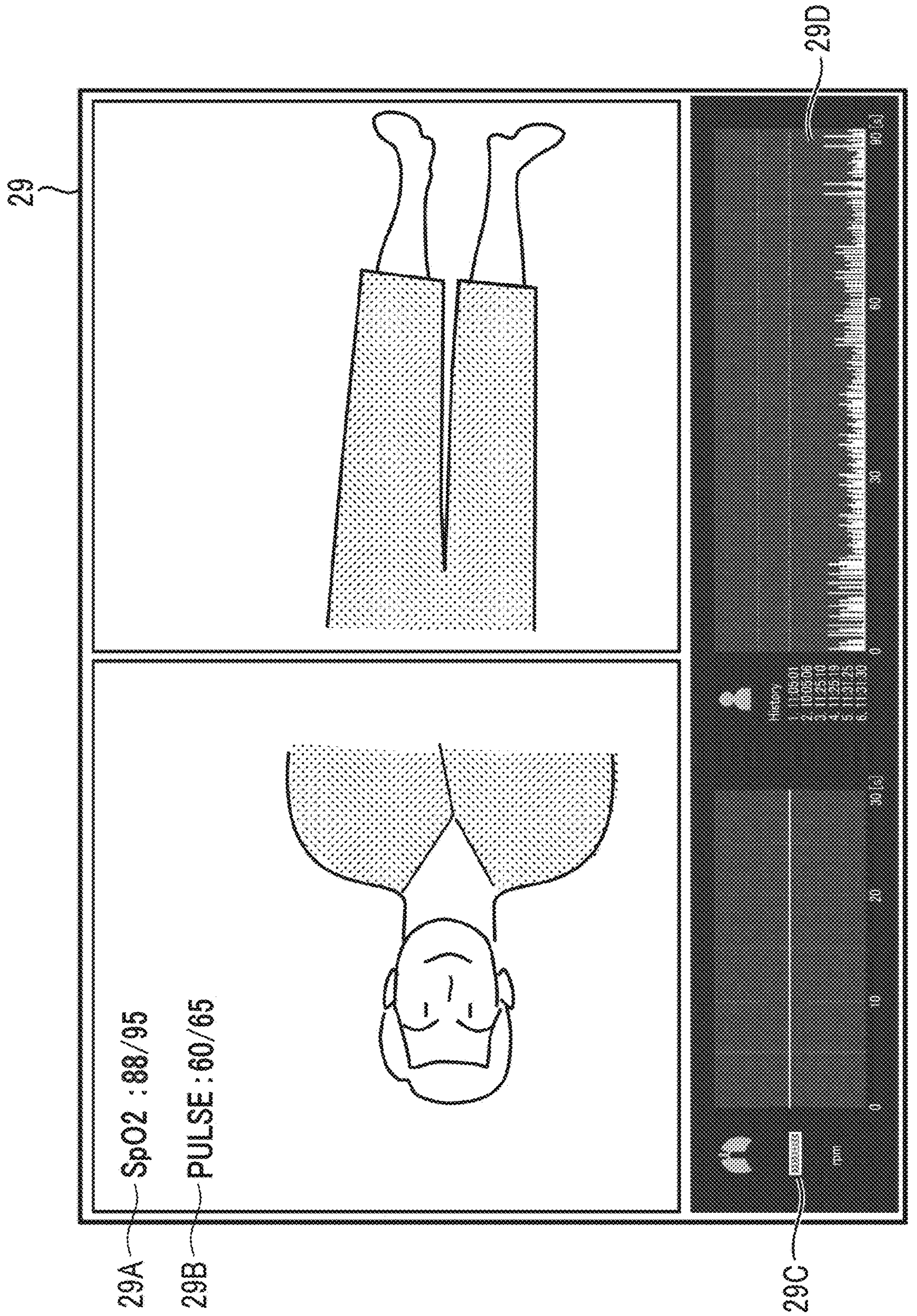

FIGS. 6 and 7 are views showing another example of the display screen of the display device that displays the vital information and the like, respectively, and show a case in which the vital information is changed with respect to the vital information at the start of the examination shown in FIG. 5.

In the example shown in FIG. 6, a state is shown in which the pulse rate 29B of the subject 5 is increased and the respiratory rate 29C is increased.

In the example shown in FIG. 7, the blood oxygen saturation concentration (SpO2) 29A of the subject 5 is decreased, and the respiratory rate 29C is in a state in which it is not measurable "–" and the respiration is stopped.

It is preferable that the vital information having a significant change changes, for example, a color or brightness on the display screen of the display device 29 so that the operator 32 can pay attention to the vital information.

Configuration Diagram of Medical Image Diagnostic System

Figure 8:
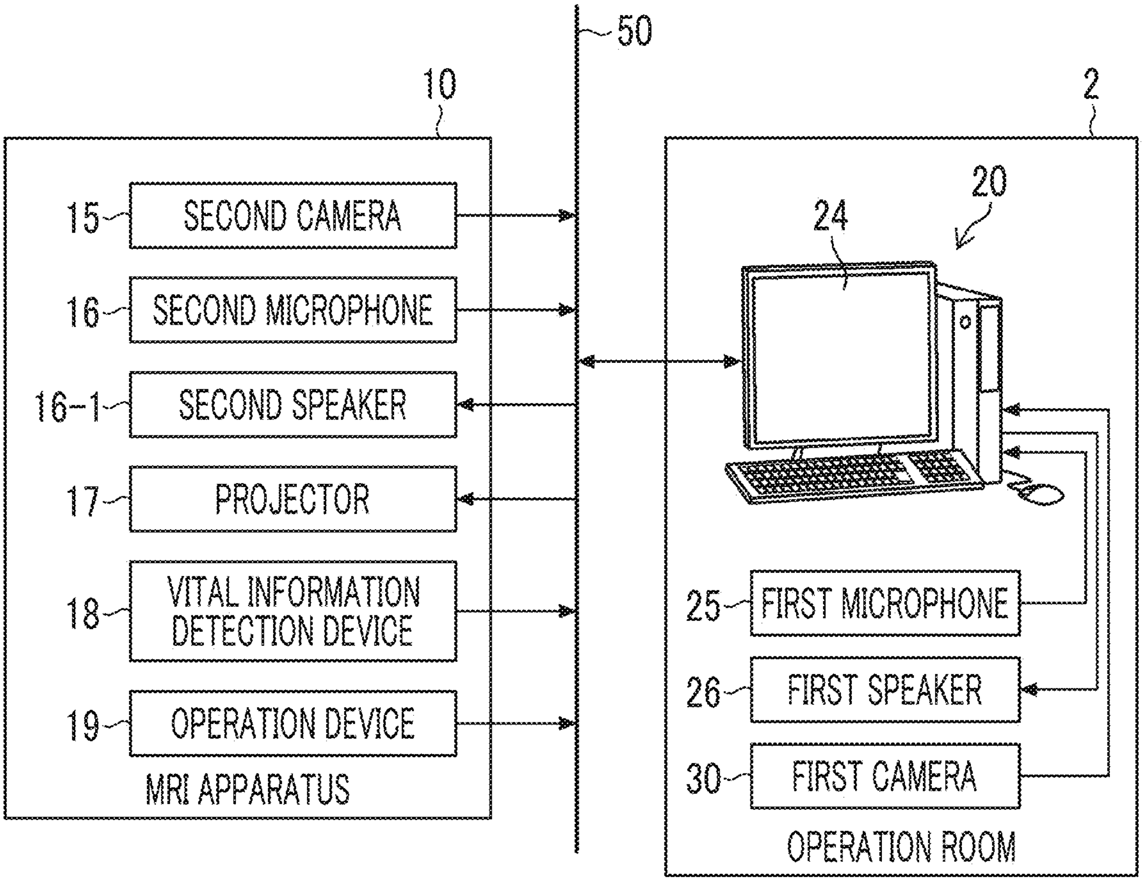
FIG. 8 is a configuration diagram of the medical image diagnostic system according to the embodiment of the present invention.

FIG. 8 is a configuration diagram of the medical image diagnostic system according to the embodiment of the present invention.

The medical image diagnostic system shown in FIG. 8 is configured such that the second camera 15, the second microphone 16, a second speaker 16-1 (see FIG. 18), the projector 17, the vital information detection device 18, an operation device 19 described below, an imaging unit (not shown) including a pulse sequence unit of the MRI apparatus 10, and the like that are provided in the MRI apparatus 10, the signal processing apparatus 20 in the operation room 2 are connected to each other via the network 50 such as a local area network (LAN).

Figure 9:
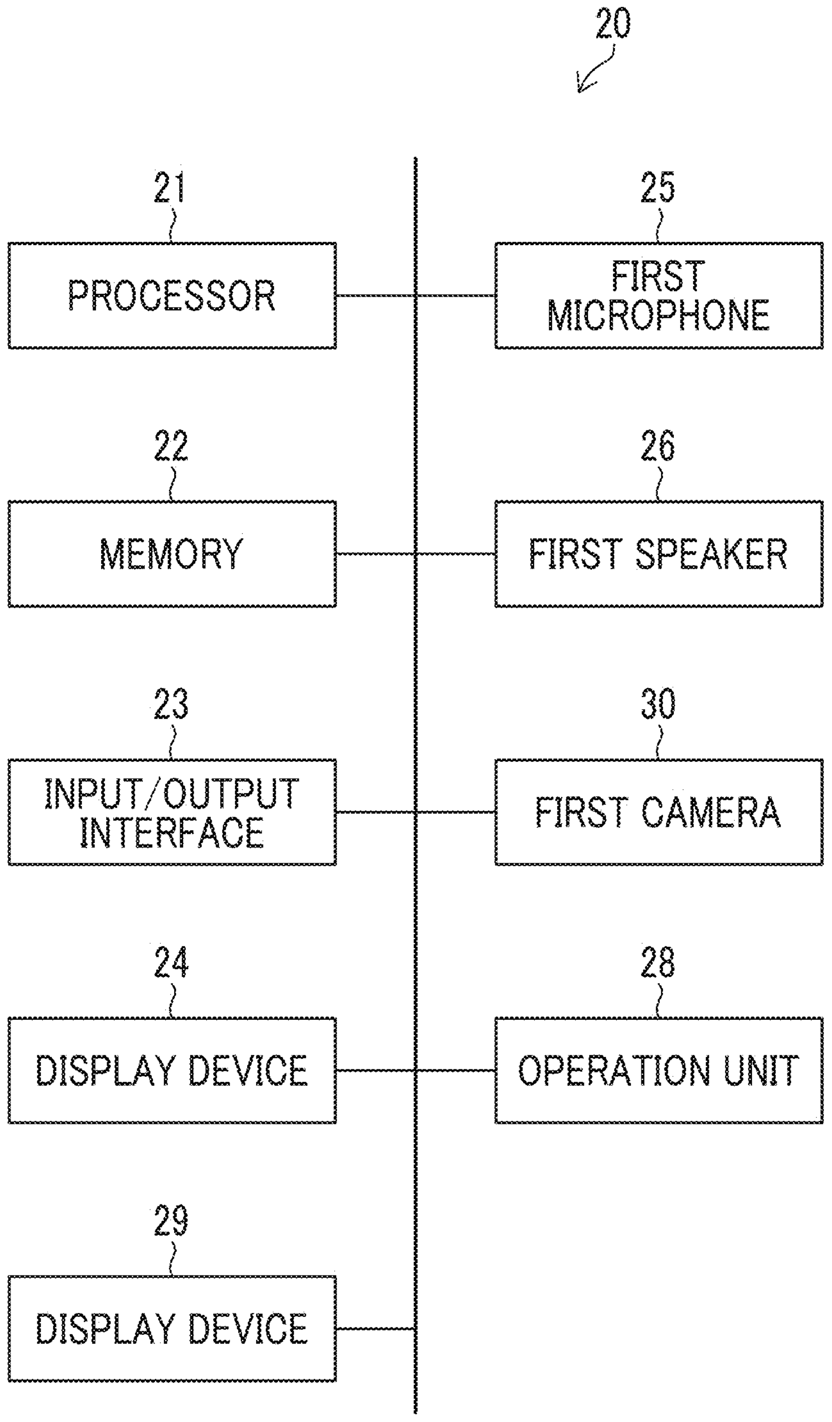
FIG. 9 is a block diagram showing an embodiment of hardware of a signal processing apparatus, which is a main device constituting the medical image diagnostic system.

FIG. 9 is a block diagram showing an embodiment of hardware of a signal processing apparatus, which is a main device constituting the medical image diagnostic system.

The signal processing apparatus 20 shown in FIG. 9 is configured by a computer or the like as described above, and comprises a processor 21, a memory 22, an input/output interface 23, the display devices 24 and 29, the first speaker 26, the operation unit 28, the first camera 30, and the like.

The processor 21 is configured by a central processing unit (CPU) and the like, and integrally controls each unit of the signal processing apparatus 20 and various devices provided in the MRI apparatus 10, to implement various functions described below by executing a signal processing program stored in the memory 22.

The memory 22 is one or more memories including a flash memory, a read-only memory (ROM), a random access memory (RAM), a hard disk device, and the like. The flash memory, the ROM, and the hard disk device are non-volatile memories that store an operation system, a signal processing program that causes the processor 21 to function as the signal processing apparatus 20, various programs including a machine learning model, a video projected by the projector 17, and the like.

The RAM functions as a work area for processing by the processor 21 and temporarily stores the program and the like stored in the non-volatile memory. It should be noted that a part (RAM) of the memory 22 may be incorporated in the processor 21.

The input/output interface 23 includes a communication unit that can be connected to the network 50, a connection unit that can be connected to an external device, and the like. For example, a universal serial bus (USB), a high-definition multimedia interface (HDMI) (HDMI is a registered trademark), or the like can be applied as the connection unit that can be connected to the external device.

The processor 21 communicates with various devices provided in the MRI apparatus 10 via the input/output interface 23 and the network 50, and transmits and receives necessary information.

The display device 24 displays the MRI image, characters indicating the utterance content uttered by the subject 5 during the examination, the MRI image, and the like, and is used as a part of a graphical user interface (GUI) in a case in which an input from the operation unit 28 is received.

In addition, the display device 29 displays the video of the subject, the vital information, and the like as shown in FIG. 5. In the present example, although the two display devices 24 and 29 are provided, the information displayed by the display devices 24 and 29 may be displayed by dividing the display screen of one display device into two screens or may be displayed by switching the screens.

The first microphone 25 detects the voice uttered by the operator 32, and outputs a voice signal indicating the detected voice to the processor 21. The processor 21 performs voice recognition on the voice signal input from the first microphone 25, and projects and displays the recognized characters as a part of the video for the subject, or generates the recognized characters as the voice uttered by the operator 32 from a speaker for the subject (second speaker 16-1 shown in FIG. 18).

The first speaker 26 generates the voice uttered by the subject 5 during the examination, and in a case in which the voice signal indicating the voice uttered by the subject 5 is input from the second microphone 16, the processor 21 outputs the voice signal to the first speaker 26, and generates the voice signal as the voice uttered by the subject 5 from the first speaker 26. It should be noted that the processor 21 preferably performs filter processing on the voice signal input from the second microphone 16 to reduce the noise generated by the MRI apparatus 10.

The operation unit 28 includes a mouse, a keyboard, and the like, uses a display operation window of the display device 24, and functions as a part of the GUI that receives the input of the operator 32.

The first camera 30 images the operator 32 as shown in FIG. 4, and the processor 21 can display the video of the operator 32 captured by the first camera 30 via the projector 17.

Outline of Medical Image Diagnostic System

The medical image diagnostic system having the above configuration detects the vital information of the subject 5 during the examination, and displays a predetermined video for the subject on the video display device based on the detected vital information. In the present example, the predetermined video is projected onto the screen 17A by the projector 17.

In a specific aspect, the medical image diagnostic system determines whether or not the detected vital information or an amount of change in the vital information exceeds a first threshold value, and in a case in which the vital information or the amount of change in the vital information exceeds the first threshold value, the medical image diagnostic system projects and displays a video for confirming the intention of the subject regarding whether or not the examination using the MRI apparatus 10 can be continued, via the projector 17. As a result, the medical image diagnostic system or the operator 32 can confirm the intention of the subject 5 regarding whether or not to be able to continue the examination, and can reduce the psychological burden on the subject 5.

In addition, in another specific aspect, the medical image diagnostic system determines whether or not the detected vital information or the amount of change in the vital information exceeds a second threshold value, and in a case in which the vital information or the amount of change in the vital information exceeds the second threshold value, the medical image diagnostic system projects and displays the video of the operator 32 via the projector 17. The subject 5 can obtain a sense of security by seeing the video of the operator 32, and thus the psychological burden on the subject 5 can be reduced.

It should be noted that the first threshold value and the second threshold value may be the same threshold value or different threshold values. In addition, each of the first threshold value and the second threshold value may be set to any value by the operator 32. Further, it is needless to say that these threshold values are different depending on the type of the vital information.

Action of Medical Image Diagnostic System

The processor 21 of the signal processing apparatus 20 acquires the vital information from the vital information detection device 18, compares the vital information or the amount of change in the vital information with the threshold value (the first threshold value or the second threshold value), and in a case in which it is determined that the vital information or the amount of change in the vital information exceeds the threshold value, projects and displays the video for the subject via the projector 17.

First Example of Video Displayed on Subject Side

Figure 10:
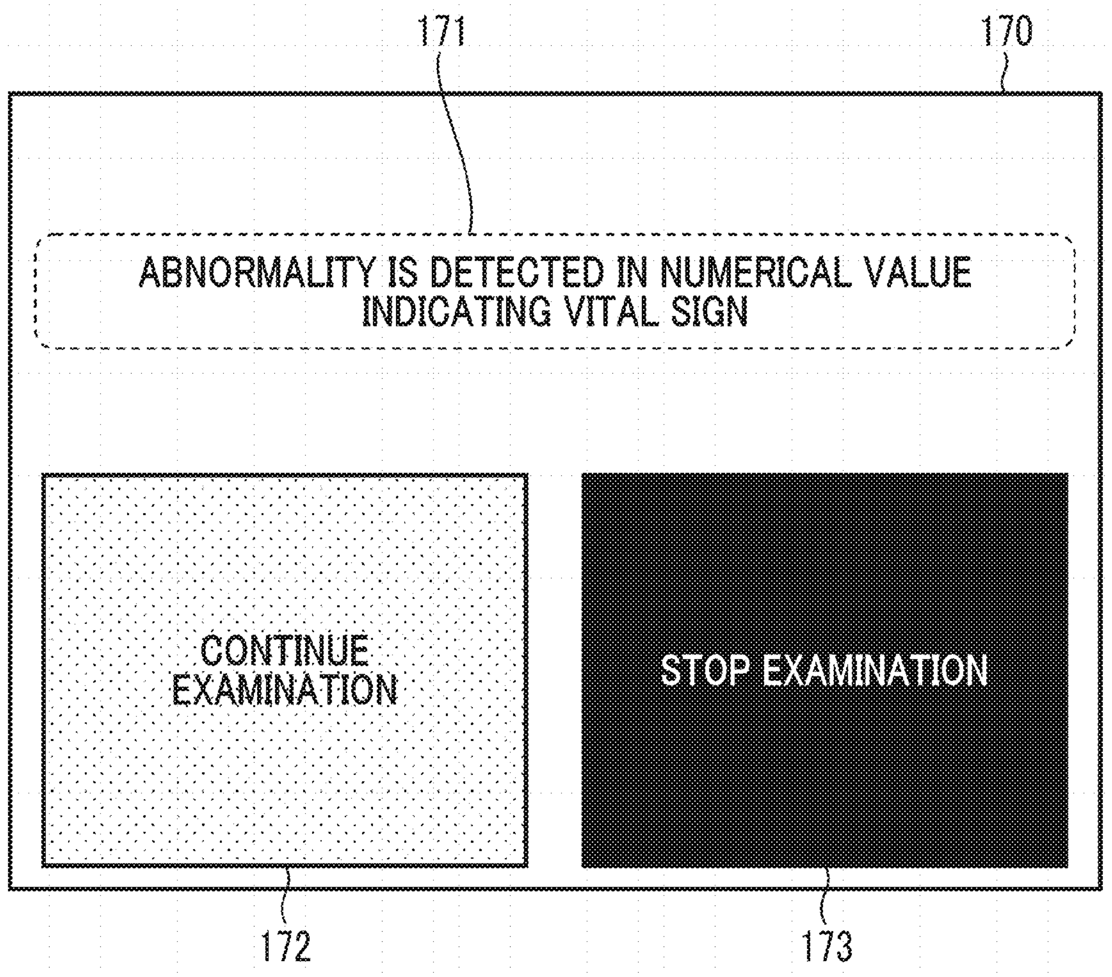
FIG. 10 is a view showing a first example of a video displayed on a subject side.

FIG. 10 is a view showing a first example of the video displayed on the subject side.

The video shown in FIG. 10 is displayed, for example, in the following cases.

A video 170 shown in FIG. 10 is a video displayed such that an abnormality of an internal device (MR-compatible pacemaker or the like) or a body is prevented from worsening during the examination, in a case in which an abnormality is detected in the body of the subject due to the vital information or the amount of change in the vital information (for example, a heartbeat or a pulse, a change in electrocardiogram information, or a change in facial expression).

In a case in which the heart rate (pulse rate) or the electrocardiogram information of the subject 5 during the examination is disturbed or the stiffness of the facial expression appears, the state of the subject is considered to be that the subject is conscious, but there is a possibility that the MR-compatible pacemaker is erroneously operated or the abnormality occurs in the body.

Therefore, in a case in which the processor 21 determines a state of the subject 5 based on the vital information or the amount of change in the vital information, the processor 21 displays the video 170 shown in FIG. 10.

The video 170 shown in FIG. 10 includes character information 171 of "The abnormality is detected in a numerical value indicating a vital sign" and an icon 172 indicating "Continue examination" and an icon 173 indicating "Stop examination" as the video for confirming the intention of the subject regarding whether or not to be able to continue the examination.

The subject 5 can transmit the intention of the subject regarding whether or not to be able to continue the examination to the medical image diagnostic system or the operator 32 by selecting the icon 172 or 173 as will be described below.

According to the example shown in FIG. 10, it is possible to perform a safer MRI examination on the subject into whom the MR-compatible device that will be increased in the future is inserted.

It should be noted that, as the vital information according to the present example, in addition to the heart rate (pulse rate) and the electrocardiogram information, a "change in facial expression" is also used as one of the amounts of change in the vital information, but the present invention is not limited to these pieces of the vital information.

Second Example of Video Displayed on Subject Side

Figure 11:
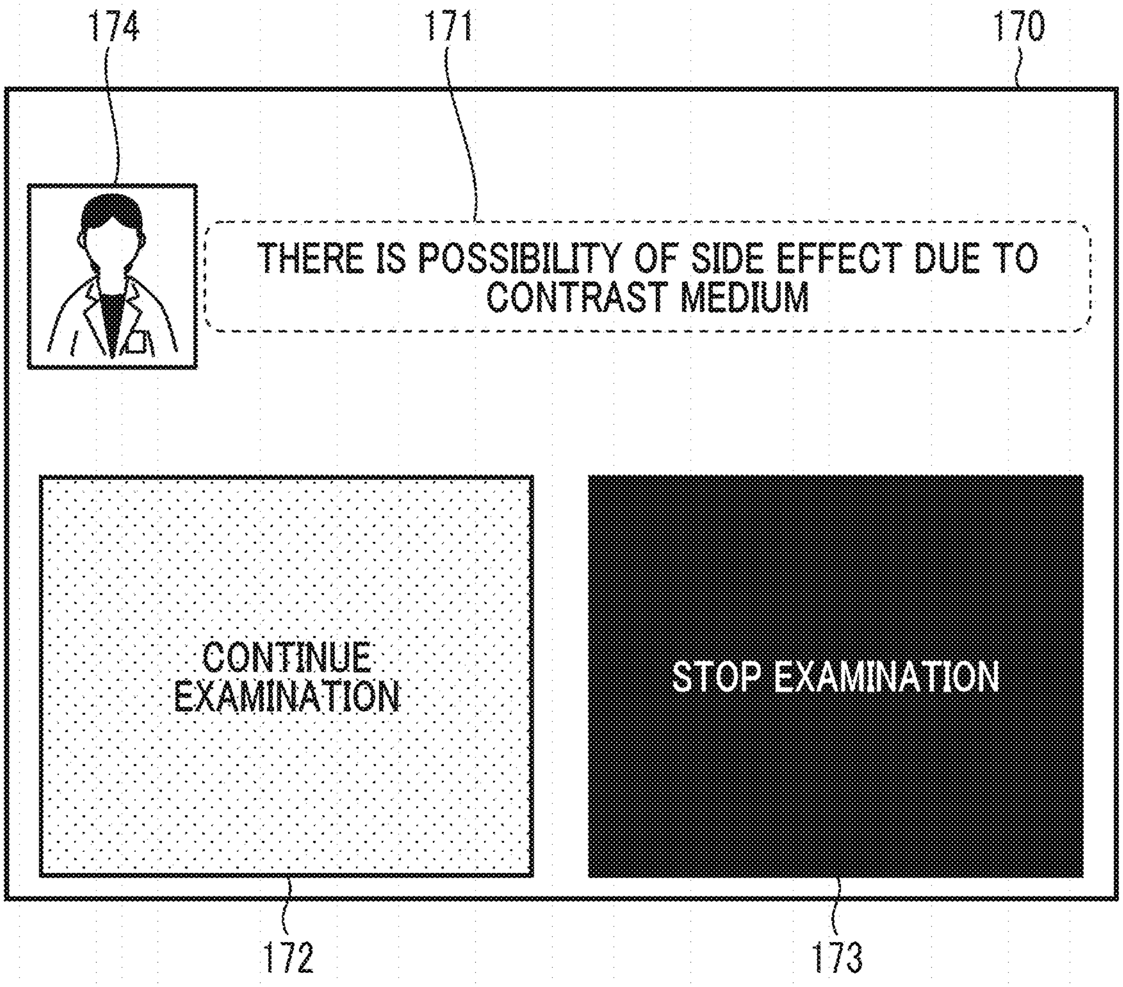
FIG. 11 is a view showing a second example of the video displayed on the subject side.

FIG. 11 is a view showing a second example of the video displayed on the subject side.

The video shown in FIG. 11 is displayed, for example, in the following case.

The video 170 shown in FIG. 11 is a video that is displayed, in a case in which a state in which a side effect of a drug is manifested in the subject 5 due to a change in the blood oxygen saturation concentration (SpO2), the pulse rate, the respiratory rate, or the face, in some cases, is detected, in order to notify the subject 5 and the operator 32 of a suspicion of the side effect and to assist the safety of the examination.

In a case in which a sudden change in the SpO2 of the subject 5, a decrease in the blood pressure (including facial pallor), or an increase in the respiratory rate appears after a contrast medium is injected, as the state of the subject 5, the subject 5 may be conscious or may be unconscious, and it is considered that there is a possibility that the side effect of the contrast medium may appear.

Therefore, in a case in which the processor 21 determines the state of the subject 5 based on the vital information or the amount of change in the vital information, the processor 21 displays the video 170 shown in FIG. 11.

The video 170 shown in FIG. 11 includes character information 171 indicating "There is a possibility of the side effect due to the contrast medium", an icon 172 indicating "Continue examination", an icon 173 indicating "Stop examination", and a video (video having a small image size) 174 showing the operator 32 imaged by the first camera 30.

The subject 5 can transmit the intention of the subject regarding whether or not to be able to continue the examination to the medical image diagnostic system or the operator 32 by selecting the icon 172 or 173.

According to the example shown in FIG. 11, it is possible to perform the examination that does not force the subject 5 and to respond to an emergency measure quickly.

Third Example of Video Displayed on Subject Side

Figure 12:
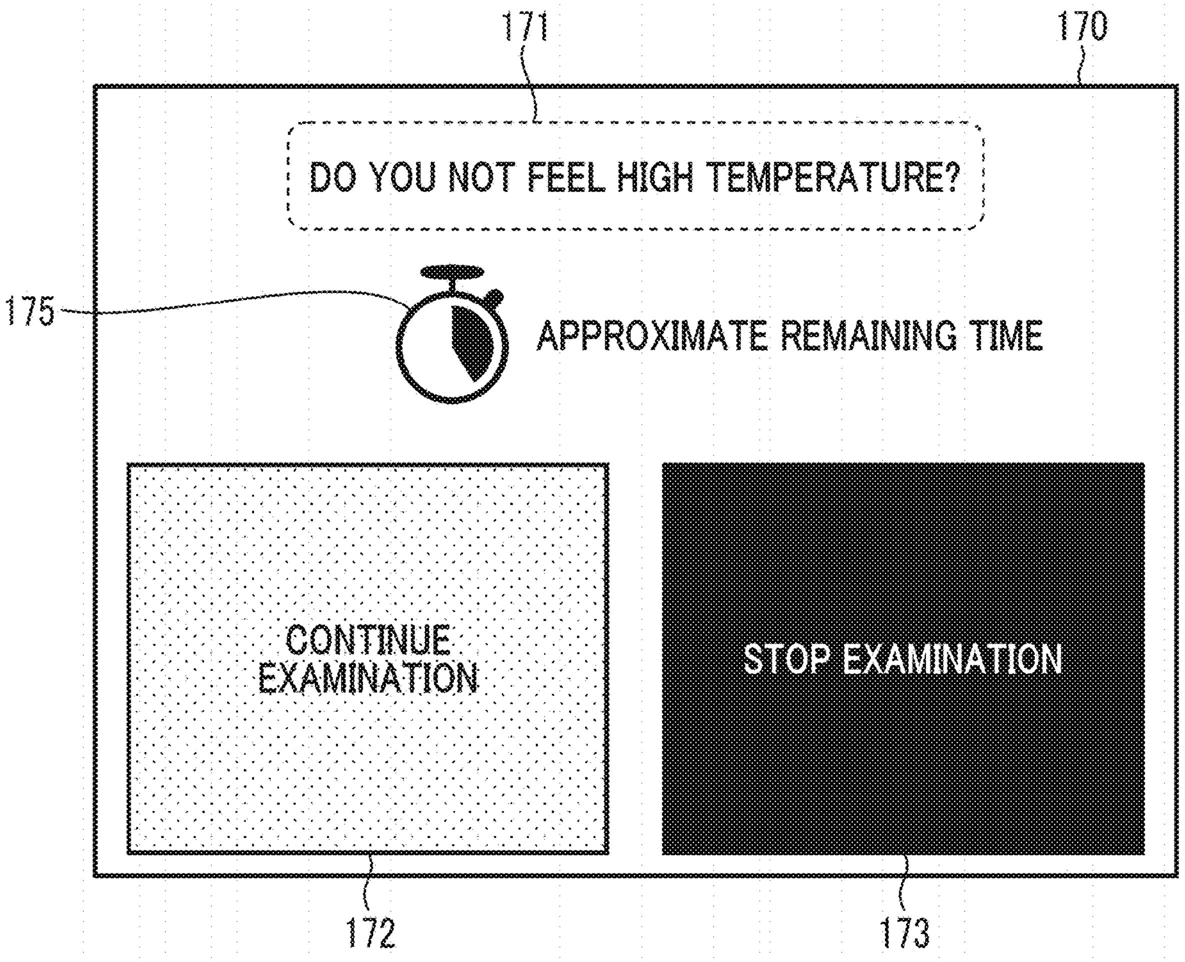
FIG. 12 is a view showing a third example of the video displayed on the subject side.

FIG. 12 is a view showing a third example of the video displayed on the subject side.

The video shown in FIG. 12 is displayed, for example, in the following cases.

The video 170 shown in FIG. 12 is a video displayed, in a case in which a feverish condition of the subject 5 and an increase in anxiety that may occur in association with the feverish condition of the subject 5 are detected due to a change in the temperature or the body temperature exerted on the body of the subject 5 by the MR imaging, in order to notify the subject 5 of the remaining examination status while confirming the feverish condition of the subject 5 to reduce the anxiety of the subject 5.

During the examination, the body temperature of the subject 5 may be rapidly increased (increase in specific absorption ratio (SAR)) depending on the type of the imaging sequence, and may be accumulated over time, so that the body around the examination part may feel hot. As the state of the subject 5, it is considered that the subject 5 is conscious, but the subject 5 may bear the heat or may have stress or anxiety to the extent that the subject 5 does not want to receive the MRI examination in the future. In an extreme case, it is considered that a mild burn may occur.

Therefore, in a case in which the processor 21 determines the state of the subject 5 based on the vital information or the amount of change in the vital information, the processor 21 displays the video 170 shown in FIG. 12.

The video 170 shown in FIG. 12 includes character information 171 of "Do you not feel a high temperature?", an icon 172 indicating "Continue examination", an icon 173 indicating "Stop examination", and 175 indicating an approximate remaining time of the examination.

The subject 5 can transmit the intention of the subject regarding whether or not to be able to continue the examination to the medical image diagnostic system or the operator 32 by selecting the icon 172 or 173.

According to the example shown in FIG. 12, it is possible to perform the examination that does not force the subject 5, and as a result, it is possible to reduce the psychological burden on the subject 5 or to always perform a safe examination.

Fourth Example of Video Displayed on Subject Side

Figure 13:
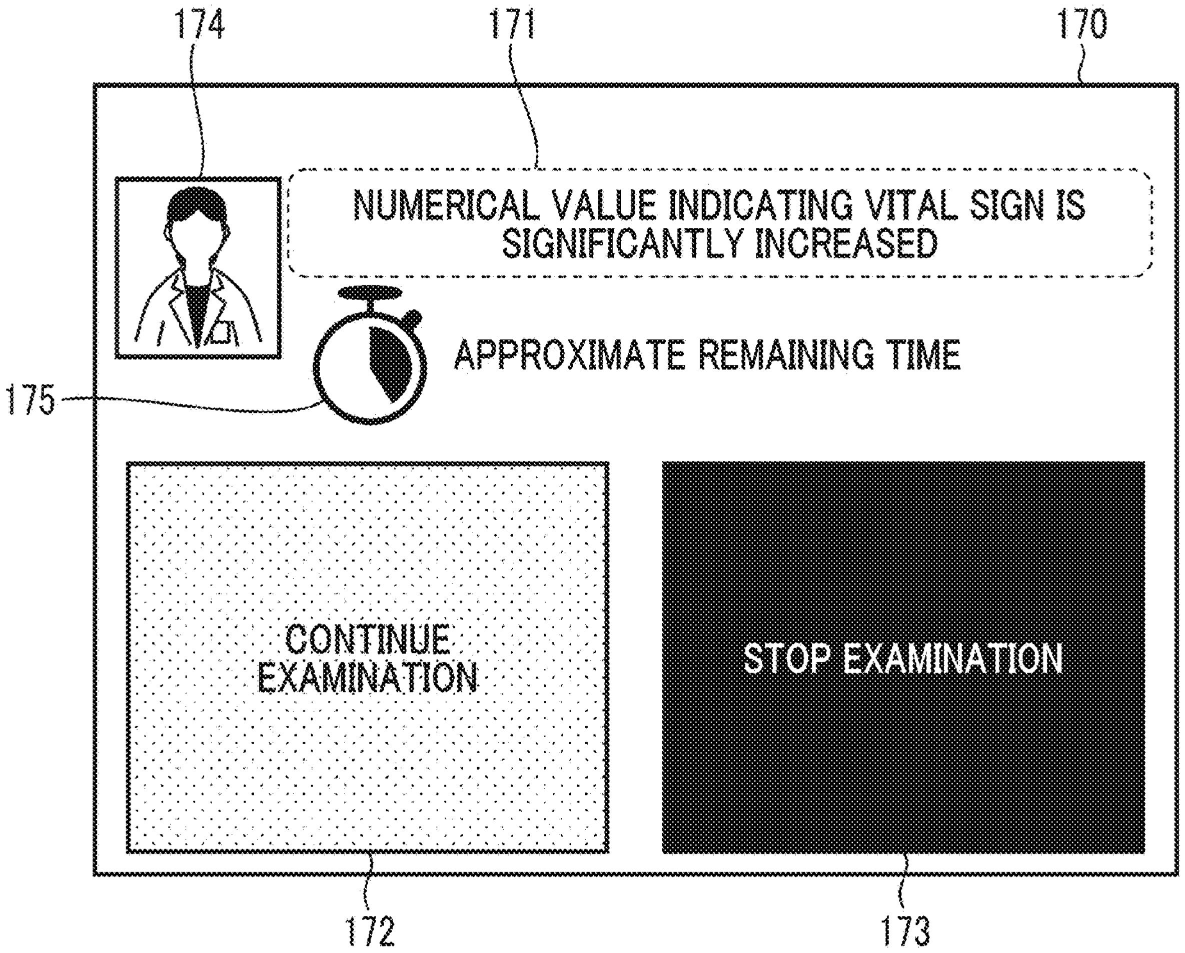
FIG. 13 is a view showing a fourth example of the video displayed on the subject side.

FIG. 13 is a view showing a fourth example of the video displayed on the subject side.

The video shown in FIG. 13 is displayed, for example, in the following cases.

The video 170 shown in FIG. 13 is a video displayed, in a case in which the increase in the anxiety of the subject 5 is detected due to the change in the heartbeat, the pulse, or the respiratory rate, in order to reduce the anxiety of the subject 5 by notifying the subject 5 of the video of the operator 32 and the remaining examination status.

In a case in which a significant increase in the heart rate, the pulse rate, or the respiratory rate of the subject 5 during the examination appears, as the psychosis of the subject 5, the subject 5 may feel anxious or nervous because the subject 5 is conscious but gradually becomes unable to endure a long-term examination or a closed space.

Therefore, in a case in which the processor 21 determines the state of the subject 5 based on the vital information or the amount of change in the vital information, the processor 21 displays the video 170 shown in FIG. 13.

The video 170 shown in FIG. 13 includes character information 171 of "The numerical value indicating the vital sign is significantly increased", an icon 172 indicating "Continue examination", an icon 173 indicating "Stop examination", a video 174 showing the operator 32 imaged by the first camera 30, and 175 indicating an approximate remaining time of the examination.

The subject 5 can transmit the intention of the subject regarding whether or not to be able to continue the examination to the medical image diagnostic system or the operator 32 by selecting the icon 172 or 173.

According to the example shown in FIG. 13, it is possible to perform the examination that does not force the subject 5, and as a result, it is possible to reduce the psychological burden on the subject 5 or to always perform a safe examination.

Fifth Example of Video Displayed on Subject Side

Figure 14:
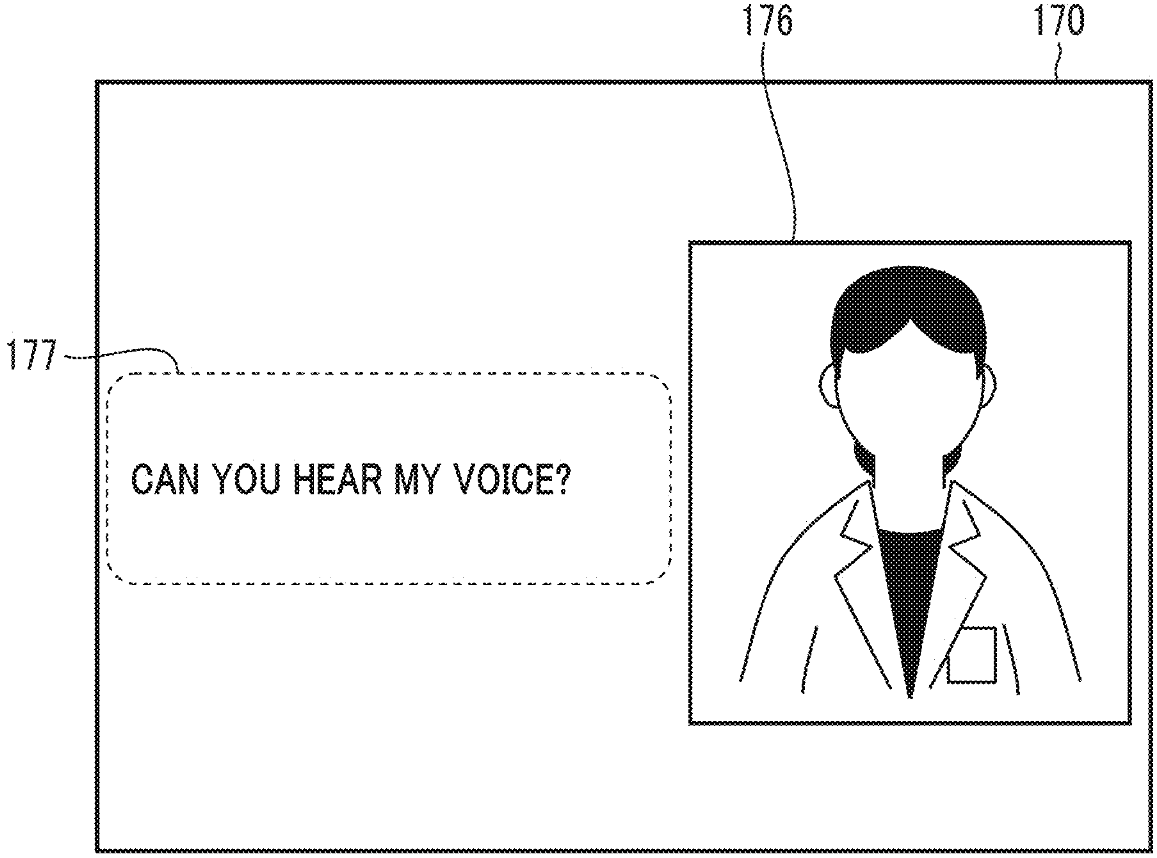
FIG. 14 is a view showing a fifth example of the video displayed on the subject side.

FIG. 14 is a view showing a fifth example of the video displayed on the subject side.

The video shown in FIG. 14 is displayed, for example, in the following cases.

The video 170 shown in FIG. 14 is a video displayed, in a case in which it is detected that the subject 5 has fallen into a serious state due to the change in the SpO2 and the respiratory rate (see FIG. 7), in order to rescue the subject 5 through the communication between the subject 5 and the operator 32.

In a case in which a significant decrease in the SpO2 or the respiratory arrest of the subject 5 appears during the examination of the subject 5, the state of the subject 5 is considered to be in a state of sudden change with a deterioration in the vital sign, and the subject 5 may be only half conscious or unconscious.

Therefore, in a case in which the processor 21 determines the state of the subject 5 based on the vital information or the amount of change in the vital information, the processor 21 displays the video 170 shown in FIG. 14.

The video 170 shown in FIG. 14 includes a video 176 showing the operator 32 imaged by the first camera 30 and character information 177 of "Can you hear my voice?".

In this case, the voice generated by the operator 32 is detected by the first microphone 25, is reproduced by the second speaker 16-1 for the subject, and conversely, the voice generated by the subject 5 is detected by the second microphone 16, and is reproduced by the first speaker 26 for the operator, so that the subject 5 and the operator 32 can communicate with each other by the voice. The second speaker 16-1 may reproduce an automatic voice set in advance in accordance with the video or the like to be displayed.

In addition, the voice generated by the operator 32 may be voice-recognized, converted into the character information, and displayed on the projected video 170, and similarly, the voice uttered by the subject 5 may be voice-recognized or the utterance content of the subject 5 may be recognized from the lip movement of the subject 5, and the recognized information may be displayed on the display device 24 or 29 for the operator. Accordingly, the subject 5 and the operator 32 can communicate with each other by the displayed character information.

According to the example shown in FIG. 14, it is possible to perform the examination that does not force the subject 5 and to respond to an emergency measure quickly.

Embodiments of Intention Detection Device and Intention Confirmation Device

As an intention detection device that detects the intention of the subject 5 for the video 170 for confirming the intention of the subject 5, the second microphone 16 that detects the voice generated by the subject 5, the second camera 15 that functions as a third camera that images the face region or a hand region of the subject 5, and the operation device 19 that receives a manual operation of the subject 5 are considered.

On the other hand, the intention confirmation device transmits a detection result detected by the intention detection device to the operator 32, and the intention confirmation device for the second microphone 16, which is the intention detection device, is the first speaker the operator that transmits the voice detected by the second microphone 16 to the operator 32.

The intention confirmation device for the second camera 15 is an utterance recognition device that analyzes the video captured by the second camera 15 and recognizes the utterance content of the subject 5 based on the movement of the lips (so-called "lip-sync") of the subject 5, or a detection device that analyzes the video captured by the second camera 15 and detects the intention of the subject 5 based on the movement of the hand or the finger of the subject 5.

Further, the intention confirmation device for the operation device 19 is a notification device that outputs an operation result of the operation device 19.

Utterance Recognition Device

Figure 15:
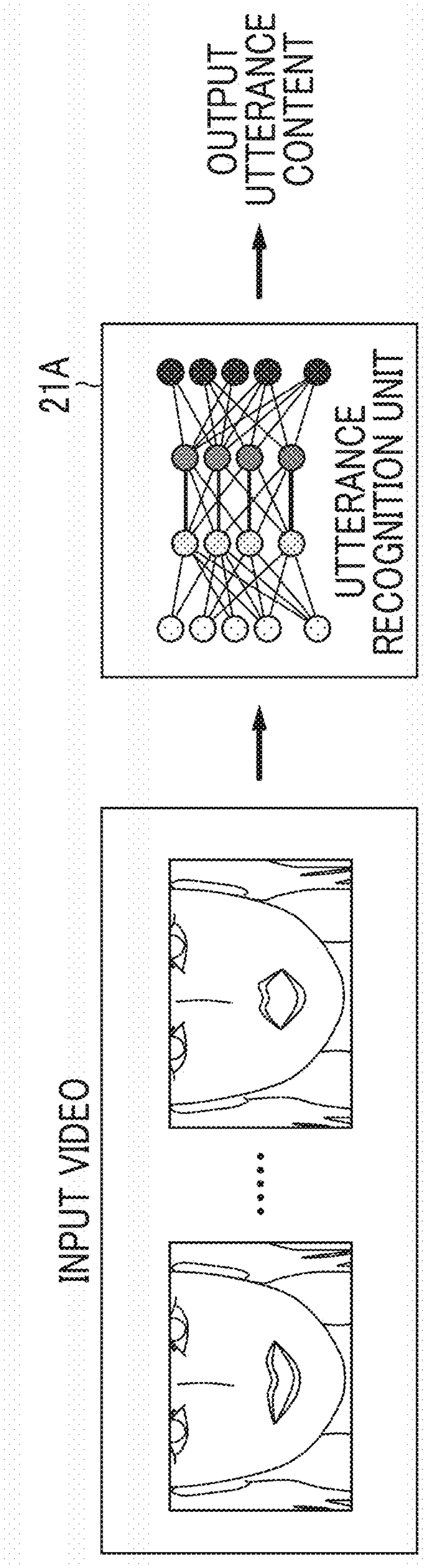
FIG. 15 is a conceptual diagram showing an embodiment of an utterance recognition device.

FIG. 15 is a conceptual diagram showing an embodiment of the utterance recognition device.

As shown in FIG. 15, the processor 21 functions as an utterance recognition device 21A.

The utterance recognition device 21A is a lip-reading unit that reads the characters from the movement of the lips of the subject 5, and in the present example, uses a trained machine learning model to input the video including the face region of the subject 5 captured by the second camera 15.

It should be noted that the processor 21 can read out and use a trained machine learning model stored in the memory 22 in advance. In addition, as the machine learning model, various learning models, such as an end-to-end deep learning network, a convolutional neural network, and a support vector machine, can be used.

In the present example, the utterance recognition device 21A outputs, one character by one character, a plurality of characters (character string indicating the utterance content) uttered by the subject 5 from the video indicating the movement of the lips of the subject 5 to be input, and preferably has a function of further performing natural language processing on the character string output from the utterance recognition device 21A to determine whether or not the character string is a meaningful utterance, or performing, in a case in which there is an error as a result of performing the natural language processing on the character string, correction to a correct utterance content.

The utterance recognition device 21A is effective in a case in which the voice of the subject 5 detected by the second microphone 16 cannot be heard (in a case in which the voice is small or in a case in which the noise during the MRI examination is large).

Detection Device

The processor 21 functions as a detection device that detects the intention of the subject 5 by analyzing the movement of the hand or the finger of the subject 5 from the video of the subject 5 captured by the second camera 15.

This detection device acquires the moving image (video) captured by the second camera 15 and detects the movement of the hand of the subject 5 in the video. The detection device combines a hand icon with the video 170 shown in FIG. 10, for example, and moves the hand icon in accordance with the movement of the hand.

The subject 5 moves his or her hand while seeing the video 170 to move the hand icon to the icon 172 of "Continue examination" or the icon 173 of "Stop examination".

The subject 5 moves the hand icon to the icon 172 of "Continue examination" or the icon 173 of "Stop examination", and then, for example, performs a tapping operation with a fingertip to transmit the intention of "Continue examination" or "Stop examination". The detection device detects the intention of the subject 5 of "Continue examination" or "Stop examination" by detecting the movement of the hand of the subject 5 from the video captured by the second camera 15.

Operation Device

Figure 16:
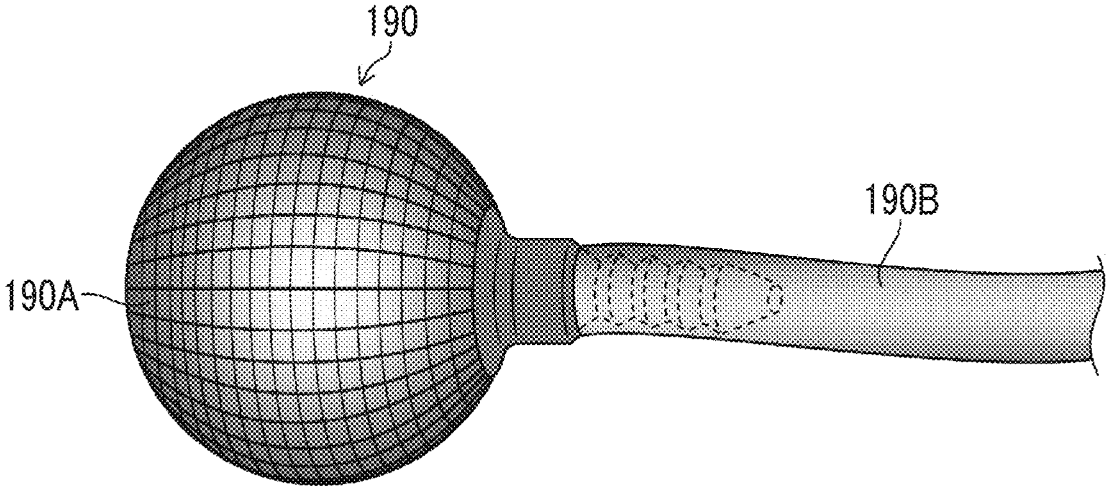
FIG. 16 is an enlarged view of a main part showing an example of an operation device operated by a subject.

FIG. 16 is an enlarged view of a main part showing an example of the operation device operated by the subject.

The operation device 19 shown in FIG. 16 is, for example, a rubber ball switch 190 that serves as an emergency switch.

The rubber ball switch 190 is possessed by the subject 5 for emergency, and the subject 5 during the examination pushes (strongly grips) the rubber ball switch 190 in an emergency. The pressure change associated with the operation of the rubber ball switch 190 is detected by a pressure switch (not shown) via a tube 190B.

In the present example, the rubber ball switch 190 is used as the intention detection device that detects the intention of the subject 5 regarding whether or not to be able to continue the examination.

For example, the subject 5 pushes the rubber ball switch 190 for a long time in a case of using the rubber ball switch 190 in a normal emergency, pushes the rubber ball switch 190 for a short time once in a case of selecting "Continue examination", and pushes the rubber ball switch 190 for a short time twice in a case of selecting "Stop examination". It should be noted that the push patterns of the rubber ball switch 190 are not limited thereto.

In a case in which the processor 21 detects that the rubber ball switch 190 is long-pressed, the processor 21 performs processing such as stopping the MRI apparatus 10.

Meanwhile, in a case in which the processor 21 detects that the rubber ball switch 190 is pushed in the push pattern indicating "Continue examination" or "Stop examination", the processor 21 functions as a detection device that outputs an operation result ("Continue examination" or "Stop examination") assigned in accordance with the push pattern.

Figure 17:
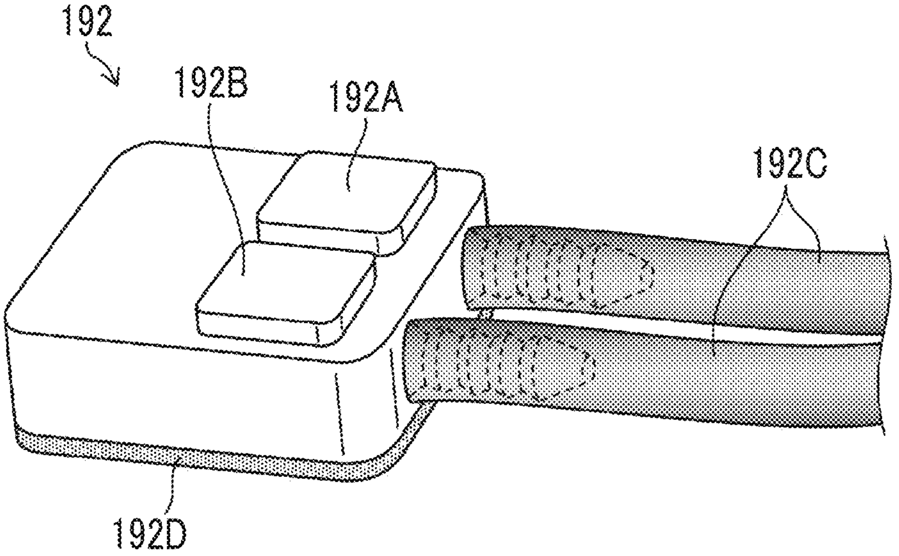
FIG. 17 is an exterior view of a main part showing another example of the operation device operated by the subject.

FIG. 17 is an exterior view of a main part showing another example of the operation device operated by the subject.

The operation device 19 shown in FIG. 17 is a push button switch 192 having push button portions 192A and 192B consisting of two air balloons.

The push button switch 192 includes two tubes 192C of which the internal pressure is changed in accordance with the push of the push button portion 192A or 192B, and the pressure change in the tube 192C is detected by a pressure sensor (not shown).

For example, the processor 21 functions as a notification device that outputs an operation result indicating "Continue examination" assigned to the push button portion 192A in a case in which it is detected that the push button portion 192A is pushed, and functions as a notification device that outputs an operation result indicating "Stop examination" assigned to the push button portion 192B in a case in which it is detected that the push button portion 192B is pushed.

Another Embodiment of Video Display Device

Figure 18:
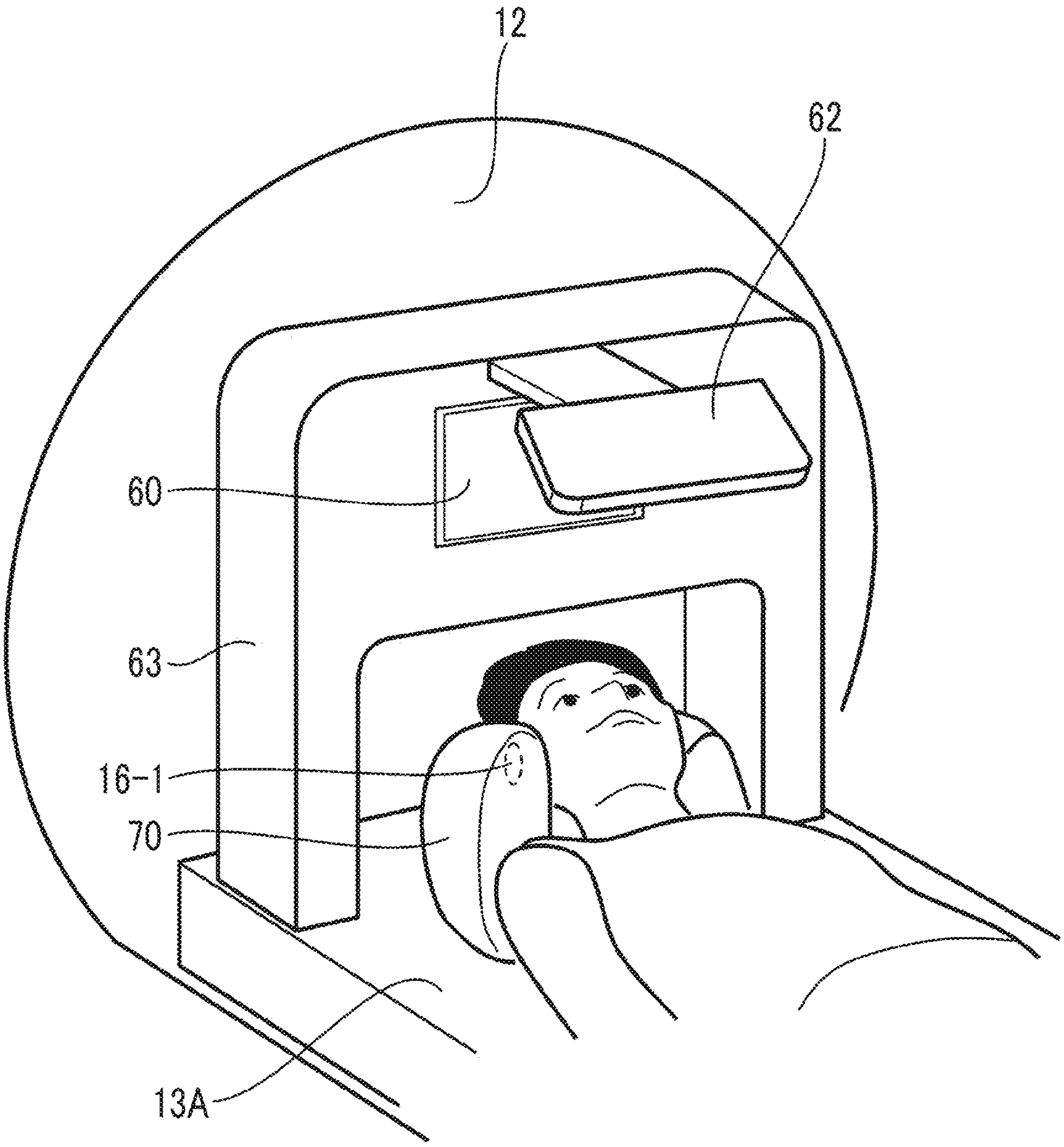
FIG. 18 is a view showing another embodiment of a video display device that displays the video in an aspect visible to the subject during an examination using the MRI apparatus.

FIG. 18 is a view showing another embodiment of the video display device that displays the video in an aspect visible to the subject during the examination using the MRI apparatus.

A video display device shown in FIG. 18 includes a projector (not shown), a rear projection screen 60 on which the video is projected from the projector, and a reflecting mirror 62 for allowing the subject 5 lying face up on the top plate 13A to visually recognize the rear projection screen 60.

The rear projection screen 60 and the reflecting mirror 62 are provided in a support member 63 attached to the top plate 13A.

In a case in which the video is projected onto the rear projection screen 60 from the projector, the subject 5 can visually recognize the video projected onto the rear projection screen 60 through the reflecting mirror 62.

The camera that images the face region of the subject 5 can be attached to an outer peripheral portion of the reflecting mirror 62. Further, the second speaker 16-1 for the subject can be embedded in a head holding tool 70 that holds the head of the subject 5 so as not to move. The second speaker 16-1 can generate the voice of the operator 32 in a case of the call with the operator 32. In addition, it is preferable that the second speaker 16-1 is a non-magnetic speaker using a piezoelectric ceramic that is a non-magnetic material for a sound emitting body.

It should be noted that the other embodiment of the video display device that displays the video in an aspect visible to the subject during the examination using the MRI apparatus is not limited to the embodiment shown in FIG. 18, and a head-up display that displays a virtual image (air image), a head-mounted display that is mounted on the head of the subject, a liquid crystal display, or an organic EL display can be used.

Display Content of Video or Like to be Displayed on Subject Side

FIG. 19 is a table showing a relationship between a detection example of the vital information, the state of the subject, and the display content of the video displayed on the subject side.

The first to fifth examples of the video displayed on the subject side have been described with reference to FIGS. 10 to 14, but the table shown in FIG. 19 includes the display contents of the video corresponding to FIGS. 10 to 14.

That is, the vital information, the state of the subject, and the display content of the video in a case in which the video shown in FIG. 10 is displayed correspond to a third item of the table shown in FIG. 19.

Similarly, FIG. 11 corresponds to a fourth item of the table shown in FIG. 19, FIG. 12 corresponds to a fifth item of the table shown in FIG. 19, FIG. 13 corresponds to a first item of the table shown in FIG. 19, and FIG. 14 corresponds to a second item of the table shown in FIG. 19.

It should be noted that the video displayed on the subject side based on the vital information is not limited to the videos shown in FIGS. 10 to 14 and the display contents shown in the table and the like of FIG. 19, and various videos can be displayed.

Operation Method of Medical Image Diagnostic System

Figure 20:
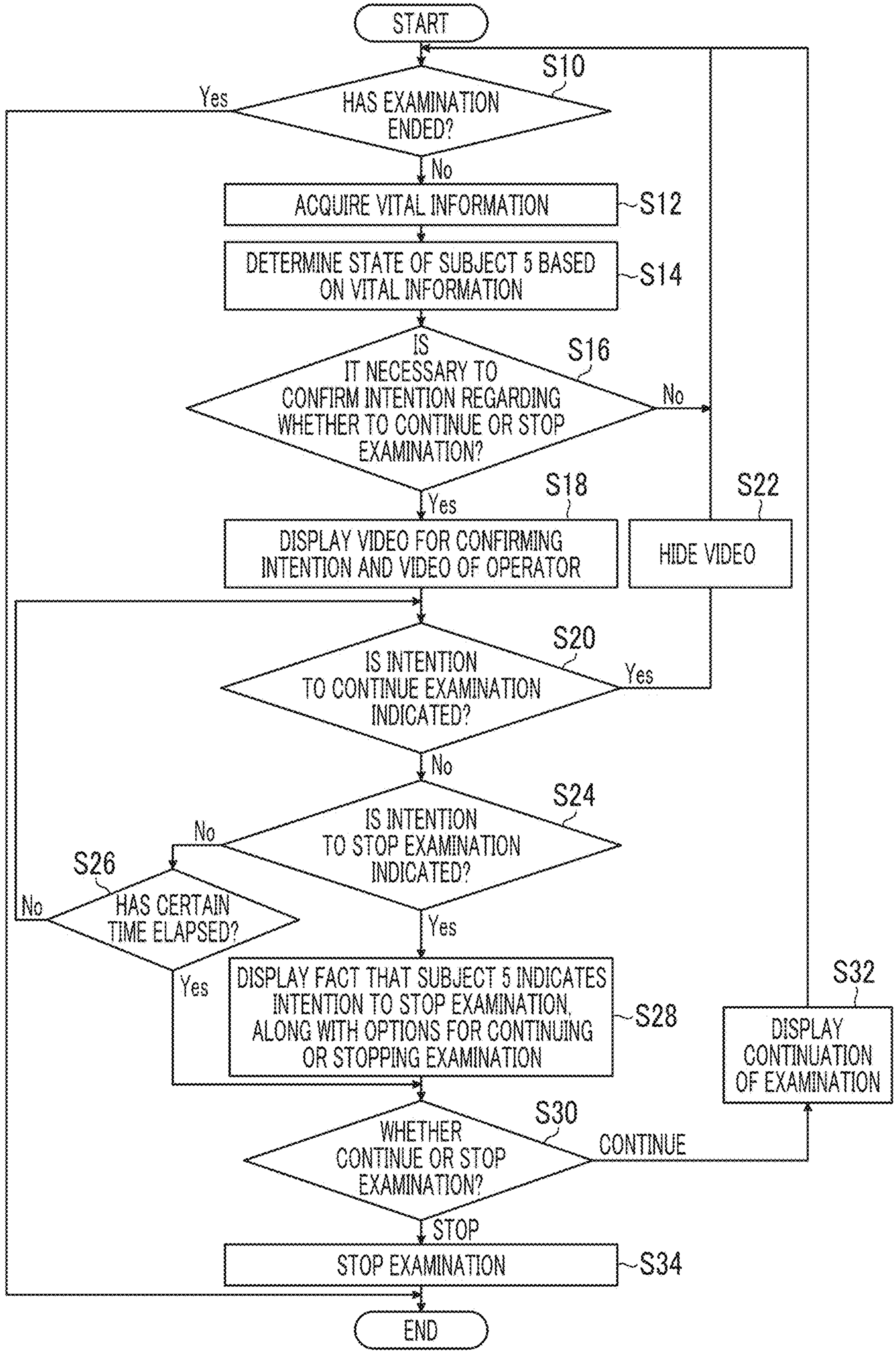
FIG. 20 is a flowchart showing another embodiment of an operation method of the medical image diagnostic system according to the embodiment of the present invention.

FIG. 20 is a flowchart showing an embodiment of the operation method of the medical image diagnostic system according to the embodiment of the present invention.

The processing of each step of the operation method of the medical image diagnostic system shown in FIG. 20 corresponds to processing performed by the processor 21 of the signal processing apparatus 20 shown in FIG. 9.

In FIG. 20, the processor 21 determines whether or not the examination of the subject 5 using the MRI apparatus 10 has ended (step S10), and in a case in which the examination has not ended, the processor 21 executes the following steps.

First, the processor 21 acquires the vital information of the subject during the examination from the vital information detection device 18 (step S12). It is preferable that the processor 21 temporarily stores the vital information of the subject 5 before the start of the examination or immediately after the start of the examination. This is to use the vital information in the examination as a reference in a case of obtaining the amount of change in the vital information in the examination.

Then, the processor 21 determines the state of the subject 5 based on the vital information acquired in step S12 (step S14, see the table in FIG. 19).

The processor 21 determines whether or not it is necessary to confirm the intention of the subject 5 regarding whether to continue the examination or to stop the examination (step S16). This determination can be performed depending on the state of the subject 5 determined in step S14. Specifically, the processor 21 compares the vital information with a preset threshold value (the first threshold value or the second threshold value) or compares the amount of change in the vital information with the threshold value set for the amount of change, determines whether or not the vital information or the amount of change in the vital information exceeds the corresponding threshold value, and confirms the intention to continue the examination or to stop the examination based on the determination result.

In step S16, in a case in which it is determined that it is necessary to confirm the intention of the subject 5, the processor 21 displays the video for confirming the intention, the video of the operator, or the like (step S18, see FIGS. 10 to 14).

Then, the processor 21 determines whether or not the subject 5 indicates the intention to continue the examination (step S20). The confirmation of the indication of the intention can be performed based on the voice of the subject detected by the second microphone 16 for the subject as described above, the movement of the lips of the subject 5, the movement of the hand or the finger of the subject 5 imaged by the second camera 15, or the manual operation of the operation device 19.

In step S20, in a case in which the subject 5 indicates the intention to continue the examination (in a case of "Yes"), the processor 21 proceeds the processing to step S10 after hiding the video displayed in step S18 (step S22). In this case, in step S16 again, it is determined whether or not it is necessary to confirm the intention of the subject 5 to continue the examination or to stop the examination, but it is preferable that a determination criterion (threshold value) in this case is set to be larger than that of the last determination. This is to prevent the hidden video from being repeatedly displayed.

In step S20, in a case in which the intention to continue the examination is not indicated, the processing proceeds to step S24, and here, the processor 21 determines whether or not the subject 5 indicates the intention to stop the examination.

In step S24, in a case in which the subject 5 indicates the intention to stop the examination (in a case of "Yes"), the processor 21 displays the fact that the subject 5 indicates the intention to stop the examination, along with the options of the examination continuation/stop on the display device 24 and/or the display device 29 that is visible to the operator 32 (step S28).

The operator 32 determines whether to continue or stop the MRI examination based on the indication of the intention of the subject 5 to stop the examination, which is displayed on the display device 24 and/or the display device 29, the vital information of the subject 5, and the like, and selects the examination continuation or stop by operating the operation unit 28 such as a mouse (step S30).

In step S30, in a case in which the operator 32 selects to continue the examination, the processor 21 displays a message indicating the examination continuation (for example, a message of "The examination will be continued") as the video for the subject (step S32), and then proceeds to step S10.

In step S32, a message "The remaining examination time is ○ minutes" may be displayed together. The remaining time may be automatically calculated from the progress of the examination, or may be manually input by the operator 32. Further, the message may be manually input by the operator 32 or may be selected from fixed phrases.

On the other hand, in step S30, in a case in which the operator 32 selects to stop the examination, the processor 21 stops the examination using the MRI apparatus 10 (step S34).

In step S24, in a case in which the subject 5 does not indicate the intention to stop the examination (in a case of "No"), the processor 21 determines whether or not a certain time has elapsed since the video is displayed (step S26).

In a case in which a certain time has not elapsed since the video is displayed, the processing proceeds to step S20. In a case in which a certain time has elapsed since the video is displayed, the processing proceeds to step S30. In step S30 in this case, since the subject 5 does not react even in a case in which the video for confirming the intention to continue the examination or to stop the examination is displayed, the operator 32 determines whether to continue or stop the examination in consideration of whether the subject 5 is only half conscious or the subject is unconscious and/or in consideration of the vital information, and selects the examination continuation or stop by operating the operation unit 28 such as a mouse.

Others

In the present embodiment, in a case in which it is not necessary to display the video for confirming the intention to continue the examination or to stop the examination of the subject 5 (for example, in a case in which the vital information is equal to or less than the threshold value or in a case in which the intention to continue the examination is indicated), a video for relaxing the subject 5 during the examination may be displayed.

In the present embodiment, for example, the hardware structure of the processing unit that executes various types of processing, such as a CPU, include the following various processors. The various processors include, for example, a central processing unit (CPU) which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform specific processing.

One processing unit may be configured by one of these various processors or by two or more processors of the same type or different types (for example, a plurality of FPGAs or a combination of a CPU and an FPGA). Moreover, a plurality of processing units may be configured by one processor. A first example of the configuration in which a plurality of processing units are configured by one processor is a form in which one processor is configured by a combination of one or more CPUs and software and functions as a plurality of processing units, as represented by a client computer or a server computer. A second example of the configuration is a form in which a processor that implements the functions of the entire system including a plurality of processing units using one integrated circuit (IC) chip is used, as represented by a system on chip (SoC). As described above, various processing units are configured by using one or more of the various processors as the hardware structure.

More specifically, the hardware structure of these various processors is an electric circuit (circuitry) obtained by combining circuit elements such as semiconductor elements.

Further, it is needless to say that the present invention is not limited to the above-described embodiments and various modifications can be made without departing from the gist of the present invention.

EXPLANATION OF REFERENCES

10: MRI apparatus
15: second camera
16: second microphone
17: projector
18: vital information detection device
19: operation device
20: signal processing apparatus
24: display device
25: first microphone
26: first speaker
30: first camera
50: network

What is claimed is:

1. A medical image diagnostic system comprising:

a projector that displays a video in an aspect visible to a subject during an examination of the subject using an image diagnostic apparatus;

a vital information detection device that detects vital information of the subject during the examination; and a processor, wherein the processor acquires the vital information from the vital information detection device, determines whether or not the vital information or an amount of change in the vital information exceeds a first threshold value, causes the projector to display a predetermined video requesting a response from the subject to indicate whether the subject intends to continue or stop the examination using the image diagnostic apparatus, in response to determining that the vital information or the amount of change in the vital information exceeds the first threshold value, and receives, from the subject, the response to the predetermined video, wherein the response indicates an intention of the subject to continue or stop the examination.

2. The medical image diagnostic system according to claim 1, further comprising:

a camera that images the operator who operates the image diagnostic apparatus, wherein the processor determines whether or not the vital information or the amount of change in the vital information exceeds a second threshold value, and causes the projector to display a video of the operator captured by the camera in a case in which it is determined that the vital information or the amount of change in the vital information exceeds the second threshold value.

3. The medical image diagnostic system according to claim 1, further comprising:

a speaker that transmits a voice, which is detected by a microphone and uttered by an operator who operates the image diagnostic apparatus, or an automatic voice to the subject during the examination.

4. The medical image diagnostic system according to claim 1, further comprising:

an intention detection device that detects an intention of the subject with respect to the video for confirming whether the subject intends to continue or stop the examination, and an intention confirmation device that transmits a detection result detected by the intention detection device to an operator who operates the image diagnostic apparatus.

5. The medical image diagnostic system according to claim 4, wherein the intention detection device is another microphone that detects a voice of the subject during the examination, another camera that images the subject, or an operation device operated by the subject, and the intention confirmation device is another speaker that transmits the voice detected by the another microphone to the operator who operates the image diagnostic apparatus, or the intention confirmation device is the processor that further analyzes a movement of lips of the subject from a video of the subject captured by the another camera to recognize an utterance content of the subject, analyzes a movement of a hand or a finger of the subject from the video of the subject captured by the another camera to detect the intention of the subject, or outputs an operation result of the operation device.

6. The medical image diagnostic system according to claim 1, wherein the vital information of the subject is one or more of electrocardiogram information, a heart rate, a blood oxygen saturation concentration, a respiratory rate, a blood pressure, or a body temperature.

7. The medical image diagnostic system according to claim 1, wherein the vital information detection device includes a camera that images the subject during the examination, and analyzes an image captured by the camera to detect at least one of a heart rate or a respiratory rate of the subject.

8. The medical image diagnostic system according to claim 1, wherein the vital information detection device includes at least one of an electrocardiogram (ECG) sensor that detects electrocardiogram information and/or a heart rate, a peripheral oxygen saturation (SpO2) sensor that measures a blood oxygen saturation concentration, a bellows that detects a respiratory rate, a pressure sensor that detects a blood pressure, an optical camera that is able to detect a body temperature, an infrared camera, or a thermography.

9. The medical image diagnostic system according to claim 1, wherein the vital information detection device is a signal processing apparatus that detects the vital information based on an image captured by the image diagnostic apparatus, an NMR signal obtained from a magnetic resonance imaging apparatus in a case in which the image diagnostic apparatus is the magnetic resonance imaging apparatus, or a pulse sequence.

10. The medical image diagnostic system according to claim 1, wherein the projector performs projection onto a screen visible to the subject, a head-up display, a head-mounted display, a liquid crystal display, or an organic EL display.

11. The medical image diagnostic system according to claim 1, wherein the image diagnostic apparatus includes a magnetic resonance imaging apparatus, an X-ray computed tomography (CT) apparatus, a positron emission tomography (PET) apparatus, a radiation therapy apparatus, or a particle beam therapy apparatus.

12. An operation method of a medical image diagnostic system including a projector that displays a video in an aspect visible to a subject during an examination of the subject using an image diagnostic apparatus, a vital information detection device that detects vital information of the subject during the examination, and a processor, the operation method comprising:

acquiring, via the processor, the vital information of the subject from the vital information detection device;

determines, via the processor, whether or not the vital information or an amount of change in the vital information exceeds a first threshold value;

causing, via the processor, the projector to display a predetermined video requesting a response from the subject to indicate whether the subject intends to continue or stop the examination using the image diagnostic apparatus, in response to determining that the vital information or the amount of change in the vital information exceeds the first threshold value; and receiving, via the processor, the response to the predetermined video from the subject, wherein the response indicates an intention of the subject to continue or stop the examination.

13. The operation method of a medical image diagnostic system according to claim 12, wherein a camera that images an operator who operates the image diagnostic apparatus is further included, and the operation method further comprises:

determining, via the processor, whether or not the vital information or the amount of change in the vital information exceeds a second threshold value; and causing, via the processor, the projector to display a video of the operator captured by the camera in a case in which it is determined that the vital information or the amount of change in the vital information exceeds the second threshold value.

14. A video display system comprising:

a projector that displays a video in an aspect visible to a subject during an examination of the subject using an image diagnostic apparatus;

a vital information detection device that detects vital information of the subject during the examination; and a processor, wherein the processor acquires the vital information from the vital information detection device, determines whether or not the vital information or an amount of change in the vital information exceeds a first threshold value, causes the projector to display a predetermined video requesting a response from the subject to indicate whether the subject intends to continue or stop the examination using the image diagnostic apparatus, in response to determining that the vital information or the amount of change in the vital information exceeds the first threshold value, and receives, from the subject, the response to the predetermined video, wherein the response indicates an intention of the subject to continue or stop the examination.

* * * * *